United States Patent [19]

Mawhirt et al.

[11] Patent Number: 4,861,553
[45] Date of Patent: Aug. 29, 1989

[54] AUTOMATIC SAMPLING SYSTEM

[75] Inventors: James A. Mawhirt, Brooklyn; Luigi Cantatore, White Plains; Joseph E. DiFlora, Eastchester, all of N.Y.; William J. C. McCandless, Ringwood, N.J.; Marvin Trieb, Irvington, N.Y.

[73] Assignee: Technicon Instruments Corporation, Tarrytown, N.Y.

[21] Appl. No.: 61,249

[22] Filed: Jun. 11, 1987

[51] Int. Cl.[4] .............................................. G01N 35/04
[52] U.S. Cl. ...................................... 422/65; 198/365; 198/803.1; 198/802; 422/99; 422/100; 422/104
[58] Field of Search ................... 198/803.01, 365, 802; 422/63–67, 99–104

[56] References Cited

U.S. PATENT DOCUMENTS

| | | | |
|---|---|---|---|
| 2,419,484 | 4/1947 | Danziger | 198/802 |
| 3,587,676 | 6/1971 | Oehlin | 422/65 |
| 4,031,998 | 6/1977 | Suzuki | 198/802 |
| 4,039,288 | 8/1977 | Moran | 422/65 |
| 4,143,751 | 3/1979 | Foster et al. | 198/802 |

Primary Examiner—Michael S. Marcus
Attorney, Agent, or Firm—Jeffrey M. Greenman

[57] ABSTRACT

The automatic sampling system includes a test apparatus for testing specific characteristics of a fluid withdrawn from a closed test tube. Stoppered test tubes are continuously and automatically delivered to the test apparatus by a conveyor system that includes a continuous linkage of test tube holders. The test tube holders have the capability of pivotal movement about a longitudinal axis of the test tube holders, and tilting movement wherein a longitudinal axis of one test tube holder tilts with respect to the longitudinal axis of another test tube holder in the linkage. The compound pivotal and tilting movement capability of the test tube holders in the linkage enable the linkage to be stacked in a fan-fold or Z-fold arrangement because of the flexible characteristics of the linkage. The linkage also has the capability of having one or more test tube holders tilted together at a group with respect to other test tube holders. Thus, the basis for a mixing operation of specific test tube holders is achieved. The conveyor system can be incorporated as a module of the test apparatus. An aspiration head for withdrawing fluid from individual stoppered test tubes in successive fashion as they are delivered by the conveyor system is also a modular addition to the test apparatus.

16 Claims, 22 Drawing Sheets

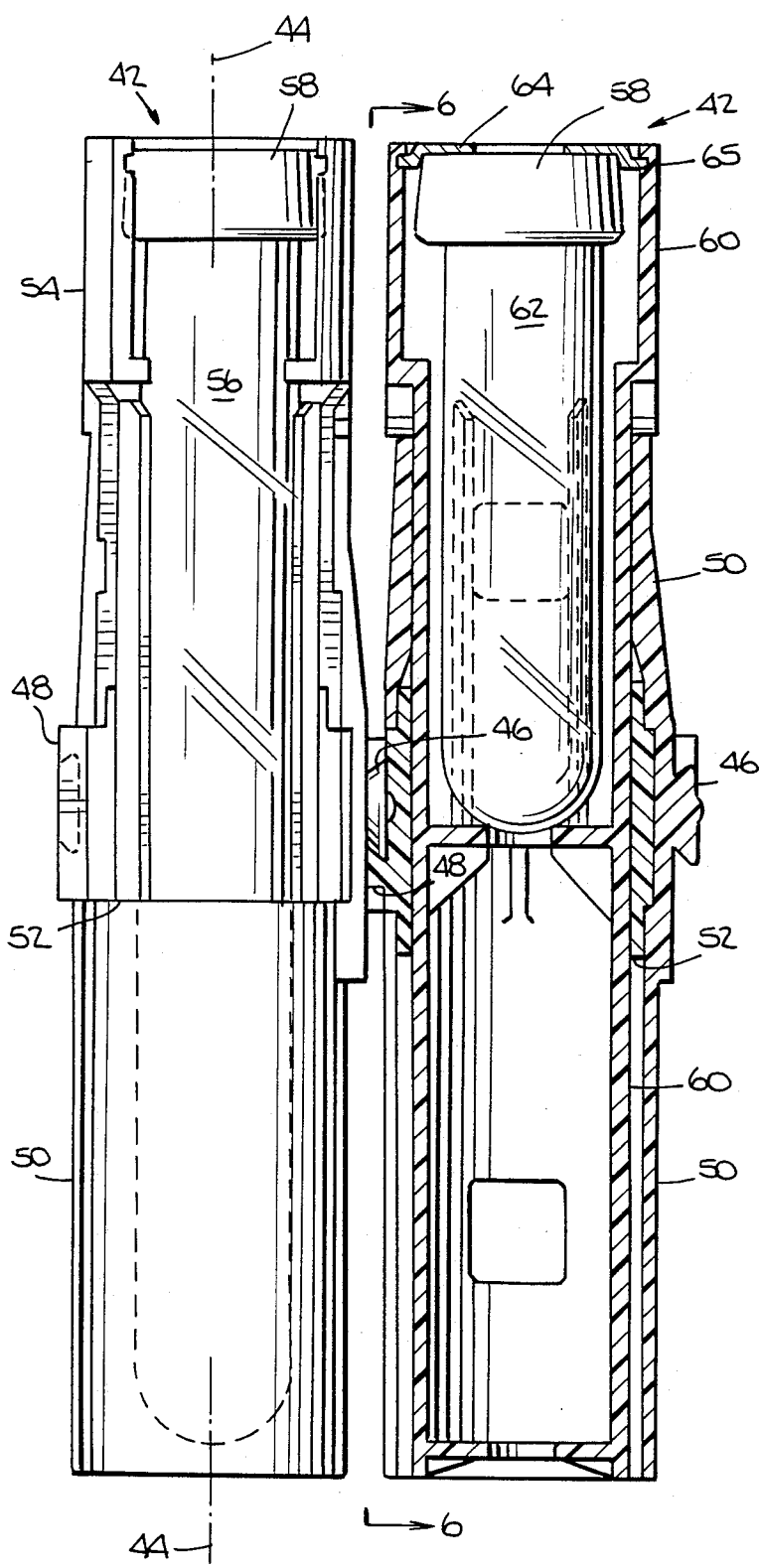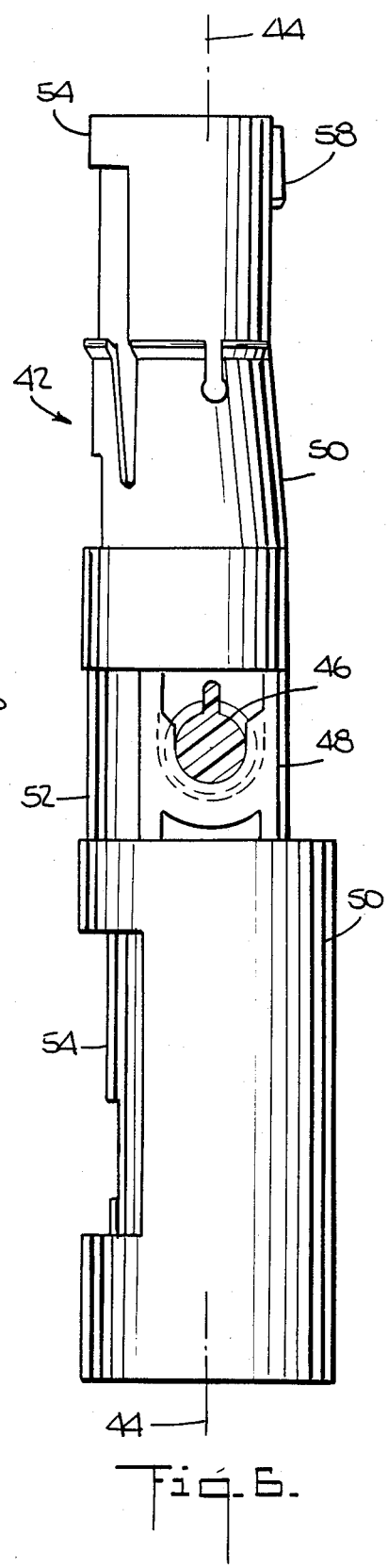

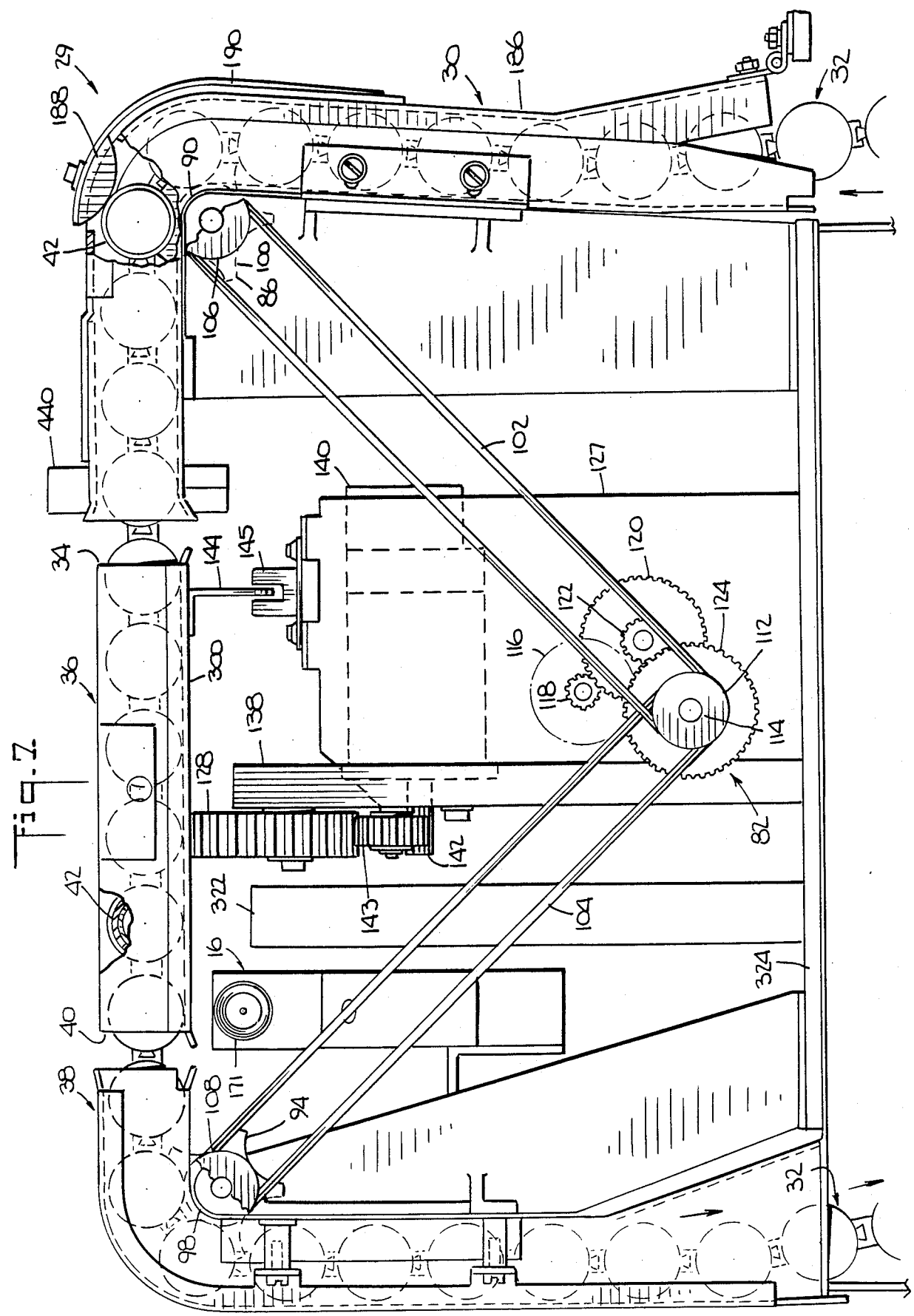

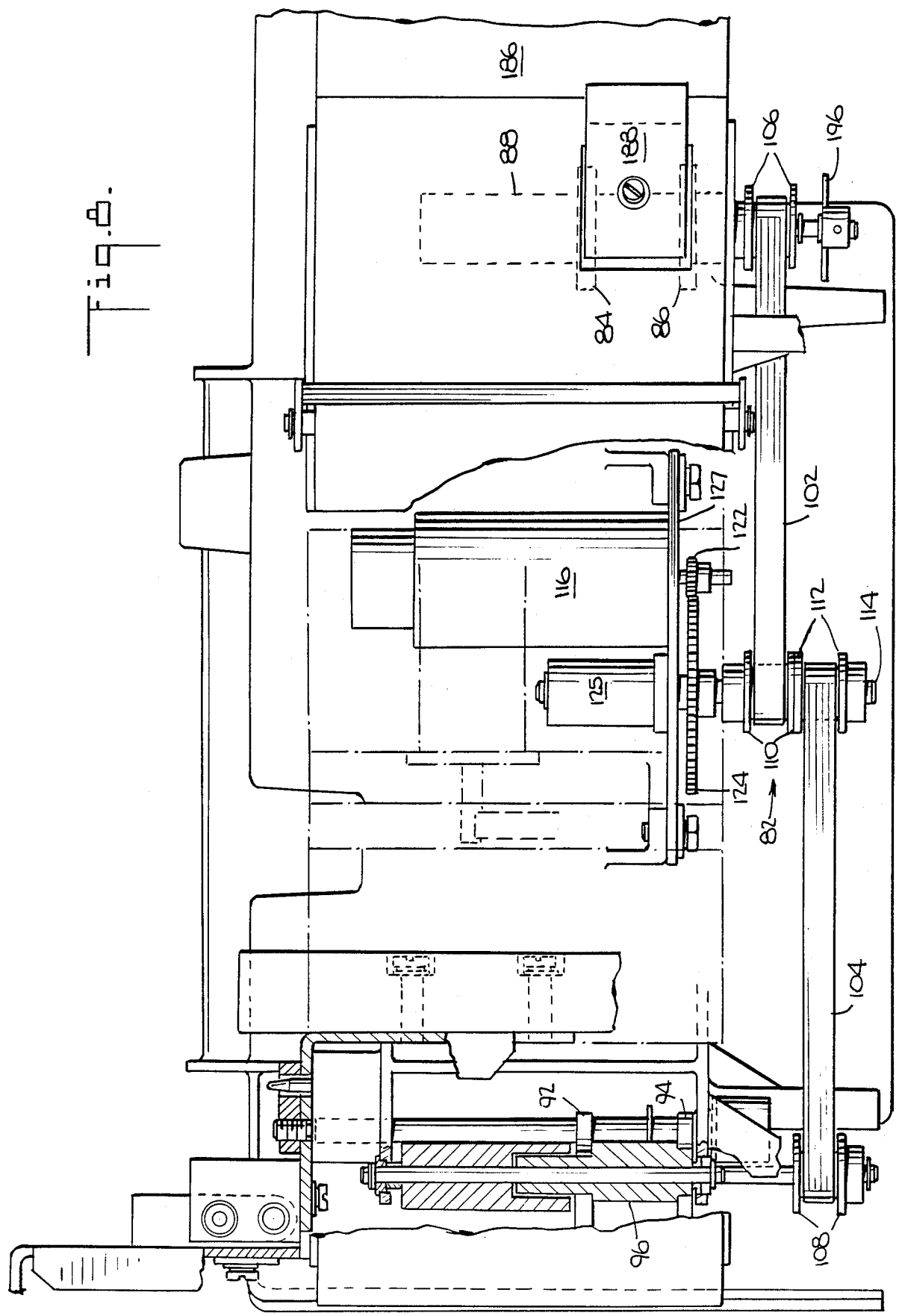

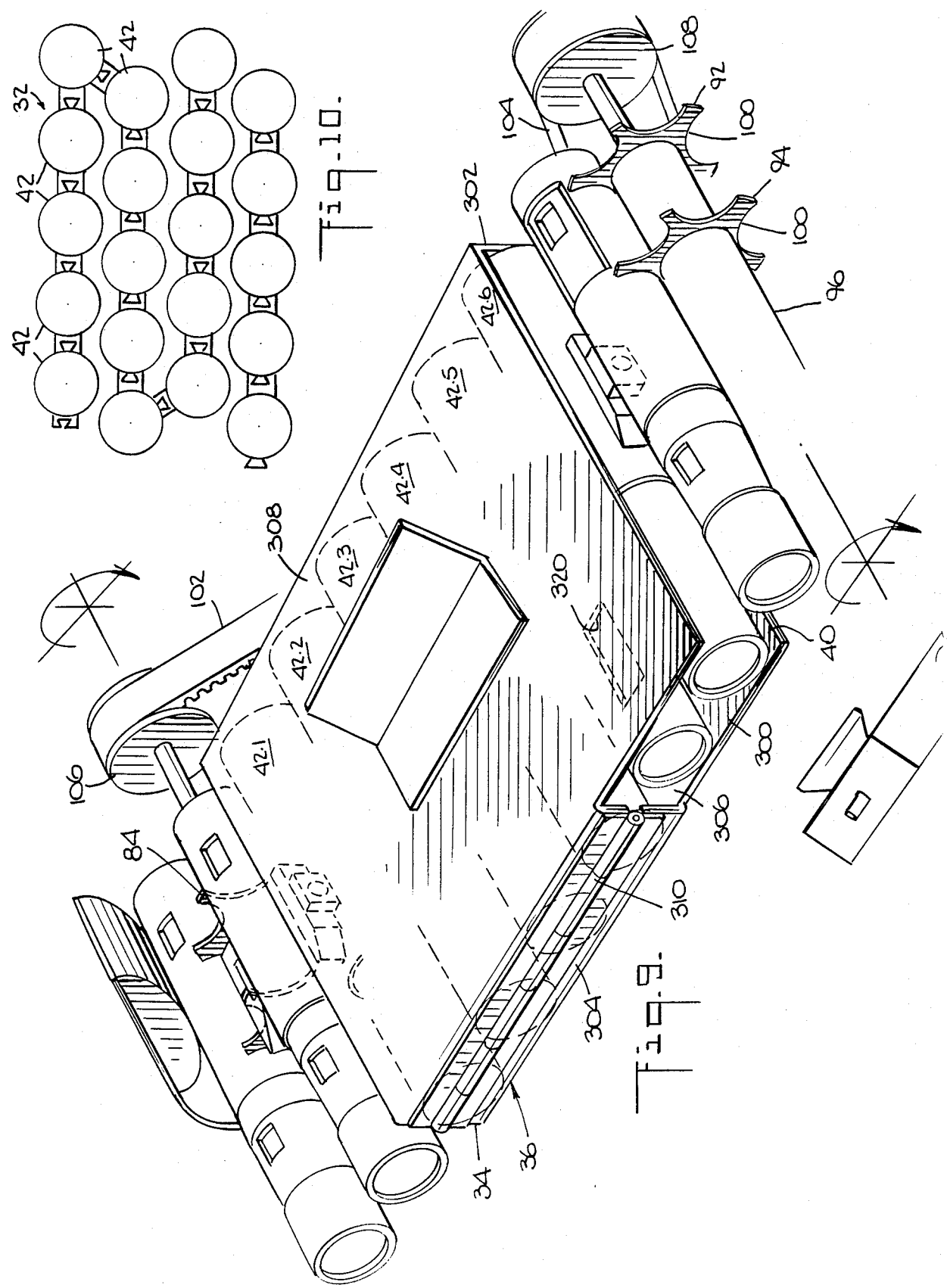

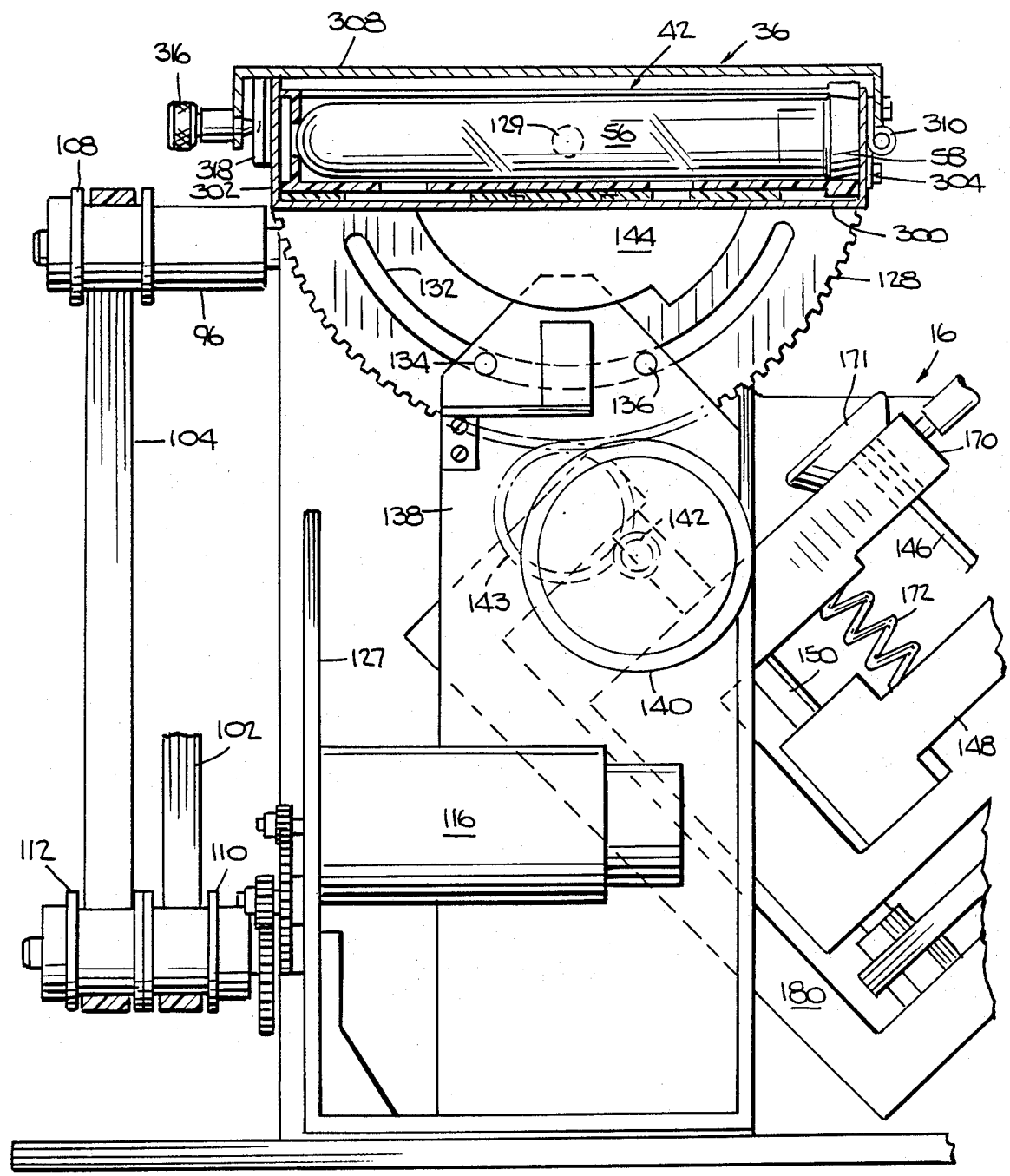

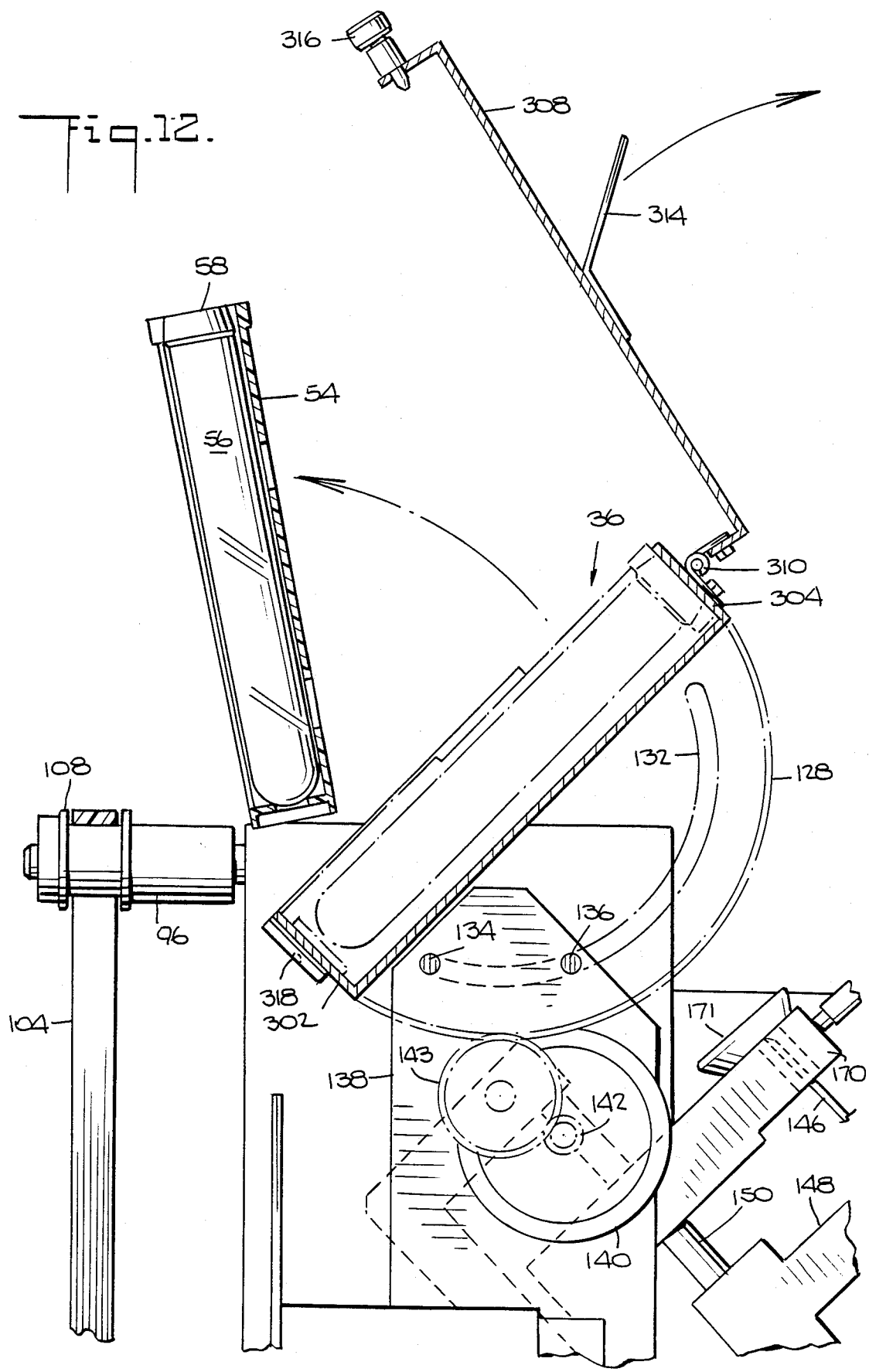

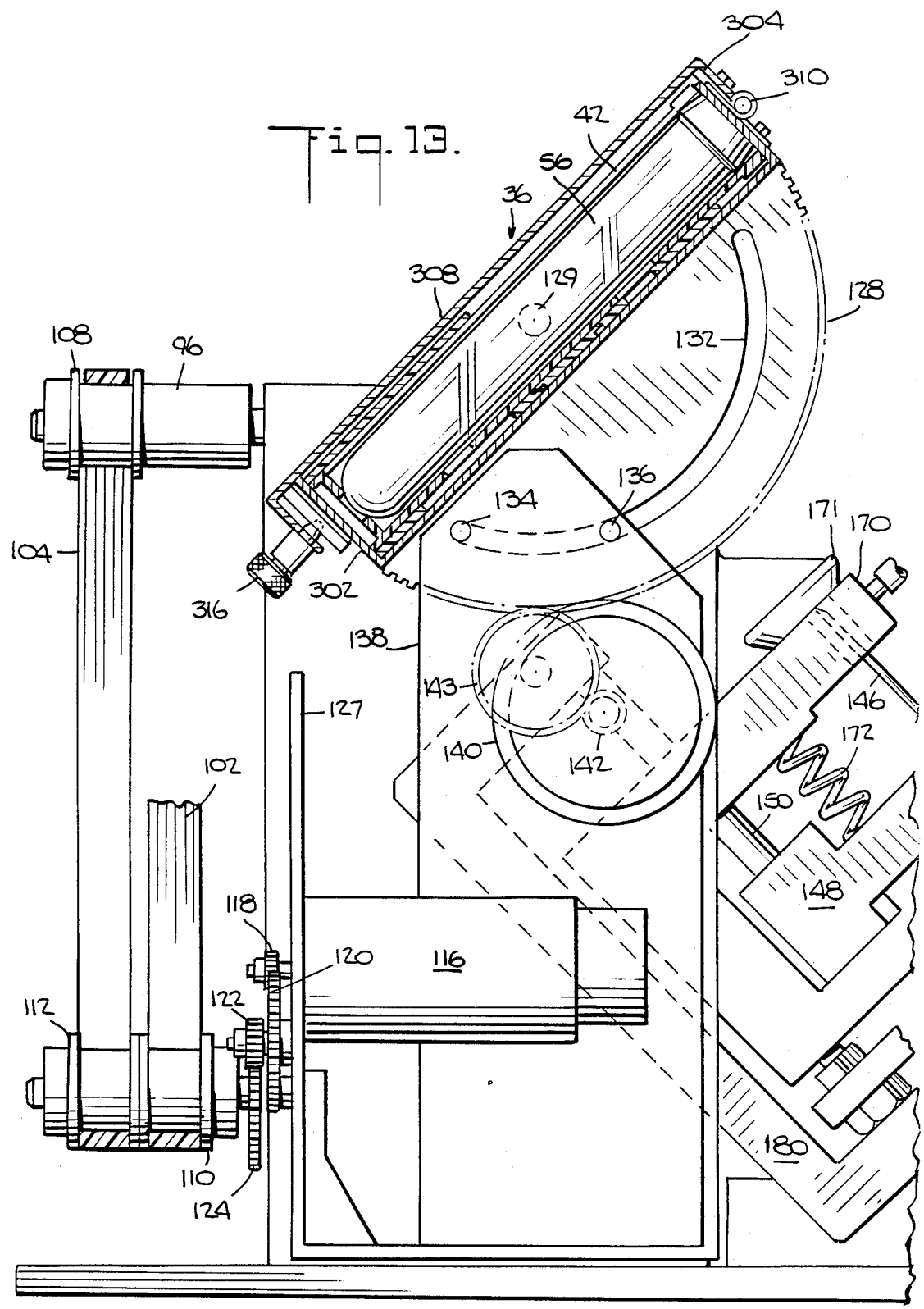

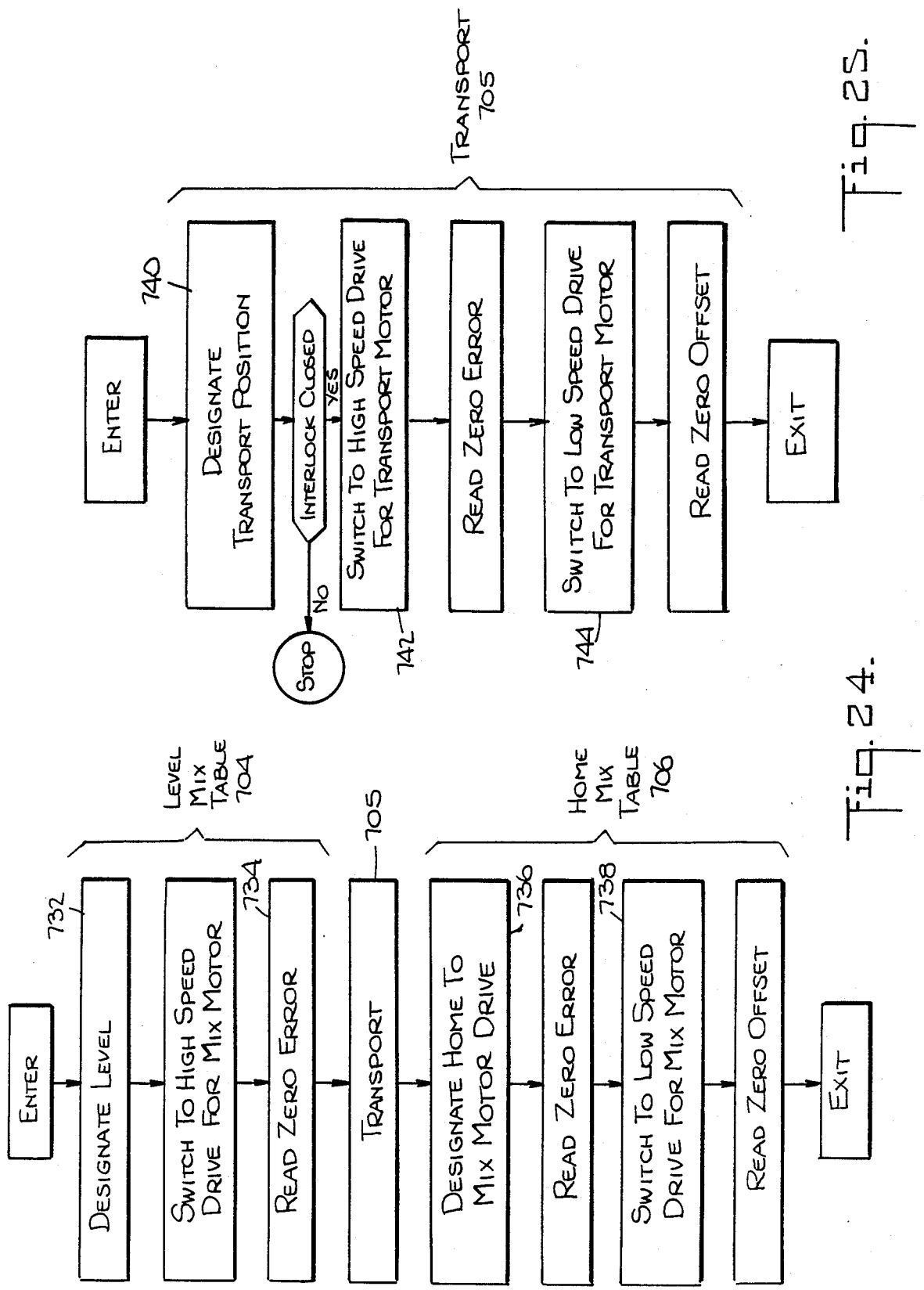

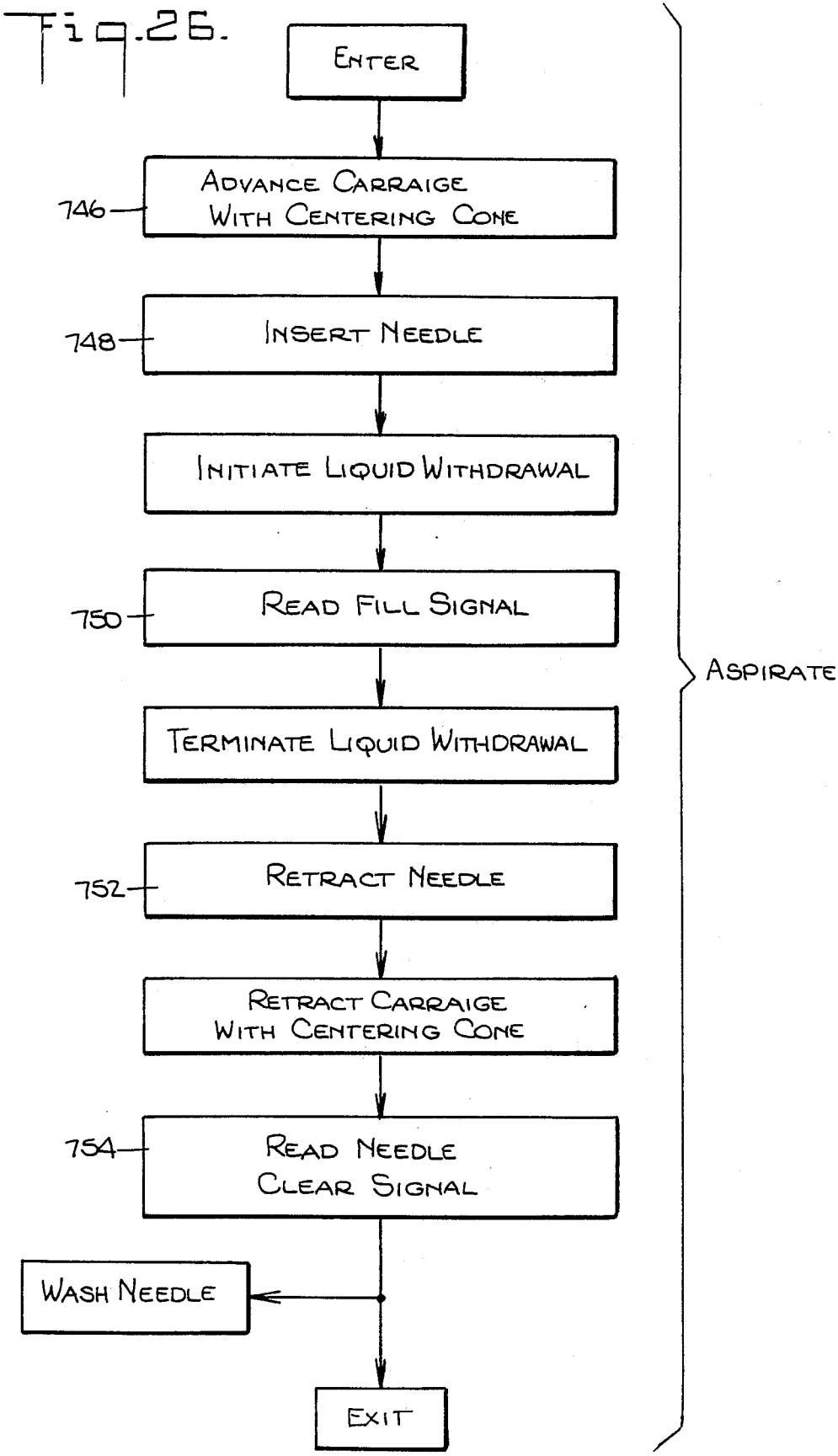

AUTOMATIC SAMPLING SYSTEM

BACKGROUND OF THE INVENTION

This invention relates to apparatus for automatically testing fluid samples such as blood, and more particularly to an automatic sampling system that receives a continuous linkage of any preselected number of test tubes for continuous, unattended analysis of the test tube contents.

In almost routine fashion, the body fluids and tissues of millions of individuals are submitted for testing each day to assess various characteristics of their body chemistry. The tests, which are conducted in hospitals, independent laboratories and doctors' offices, are often used to supplement a medical judgment, as well as provide data for other determinations. An increasing proportion of such tests are used to detect the presence of fatal diseases such as AIDS, and to screen for illicit drug use.

Known automated and computerized test apparatus can perform multiple test analyses of blood chemistry, determine the blood type and Rh factor as well as screen for syphilis and German measles. Examples of apparatus and processes for carrying out automatic blood testing are shown in U.S. Pat. Nos. 3,740,143; 3,741,875 and 4,487,700.

Many known test apparatus for testing fluid samples require manual feeding of open test tubes, necessitating the presence of an operator or technician during the performance of such tests. An important function of an operator in addition to introducing a fluid sample into a test apparatus, is to mix the sample just before it is introduced.

Thus, the development of automatic feed systems for test apparatus of the type described has become a major goal of the testing industry.

In response to this problem, U.S. Pat. No. 4,609,017 discloses a transport system for automatically transporting sealed test tubes and mixing the test tubes. In accordance with the transport system, a set number of test tubes are lined up in a rack and a plurality of such racks are stacked by an operator in the test apparatus. Each rack is automatically shifted in successive order onto a conveyor belt which moves in stepwise fashion to align a respective test tube in the rack with an aspirator that draws a fluid sample from the test tube. The conveyor belt is supported on a table that is rocked during each advancing step to mix the contents of the test tubes.

When a test tube is aligned with the aspirator, a push rod projects the test tube out of the rack against the aspirator needle. After aspiration is completed, a stripper bar retracts the protracted test tube back into the rack. The conveyor then moves another step to align the next test tube in the rack with the aspirator needle. When the complete line of test tubes in the rack have been aspirated, the rack is shifted by the conveyor into a storage space in the apparatus for eventual removal by an operator.

A primary disadvantage of the rack feed arrangement is the limited capacity in the test apparatus of stacking space for accommodating the incoming racks. Another disadvantage is that the finished racks remain stored in the apparatus until their removal by an operator. A further disadvantage is the racks are held in place on the conveyor by frictional contact between the rack and the conveyor. Thus, any slippage between the rack and conveyor will upset the indexing system movement that aligns the test tubes with the aspirator with each stepwise movement of the conveyor. Such slippage may occur when a test tube is protracted from the rack with a push rod to engage the aspirator. The push rod can upset the position of the rack on the conveyor and require the intervention of an operator to correct such malfunction. Similar slippage can occur when the stripper bar is used to retract the test tube into the rack. A still further disadvantage is that the test tube racks must be elevated onto and off the conveyor belt, thus requiring a separate elevator system. Still another disadvantage is that all test tubes in the rack must be of the same size.

A continuous feed arrangement for test tubes, as shown in U.S. Pat. No. 3,521,785, discloses test tubes connected together in chain-like fashion by using the test tubes to form the joints of the chain. Removal or breakage of one test tube will cause a break in the chain. In addition, this device does not permit the mixing of a given number of test tubes in the chain which are in proximity of a sampling station of a test apparatus.

It is thus desirable to provide an automatic test apparatus having an automatic feed system which can feed an unlimited number of test tubes in continuous fashion to a sampling station of the test apparatus, continuously identify each test tube that is being sampled, and continuously deposit the finished test tubes in a collection area. It is also desirable that the continuous feed system mix a predetermined number of the test tubes just before they are tested and that the contents of the test tube be sampled or withdrawn without moving the test tube from its transported position.

OBJECTS AND SUMMARY OF THE INVENTION

Among the several objects of the invention may be noted the provision of a novel automatic sampling system, a novel automatic sampling system having an automatic feed arrangement for continuously conveying any selected number of test tubes to a sampling station, a novel automatic sampling system having an automatic feed arrangement wherein any selected number of test tube holders can be connected together to form a continuous linkage, a novel automatic sampling system having an automatic feed arrangement which accommodates test tubes of different size, a novel automatic sampling system having an automatic feed arrangement which includes test tube holders that encapsulate and protect the test tubes being transported therein, a novel automatic sampling system having an automatic feed arrangement which provides precise indexing of test tube movement to align each test tube with an aspiration needle, a novel automatic sampling system having an automatic feed arrangement for test tubes which maintains continuity during transport, mixing and aspiration of the test tubes, and a novel method of continuously testing fluid samples.

Other objects and features of the invention will be in part apparent and in part pointed out hereinafter.

In accordance with the present invention, the automatic sampling system includes a test apparatus for automatically analyzing a sample of fluid via a plurality of tests performed by the apparatus on predetermined portions of the sample. The test apparatus is fed continuously by a conveyor system which can be modular. The conveyor system transports test tubes containing the fluid samples to a sampling or aspiration station on the test apparatus which includes an aspiration needle.

Mixing means cooperate with the conveyor system to automatically mix a predetermined number of test tubes containing the fluid samples before the test tubes are automatically aspirated in successive order.

The test tubes are transported to the sampling station in a linkage of test tube holders that are joined together to permit relative pivotal and tilting movement in radial and longitudinal directions. Thus, a single test tube holder or a group of test tube holders can be collectively tilted to provide a mixing motion that is needed before any individual test tube is aspirated.

The linkage of test tube holders remains integral before, during and after mixing as well as during aspiration of any individual test tube. The linkage can be of any selected length depending upon the number of test tube holders that are joined together. Additional test tube holders and/or additional linkages can be added as desired to the incoming linkage. Thus, a linkage of unlimited length is theoretically possible.

In the present automatic sampler, the test apparatus is adapted from a known device which normally operates on manually introduced open tube samples, yet provides the requisite number of tests on such samples. A conveyor module is provided for automatically delivering the linkage of test tube holders to the test apparatus. An aspiration module is also incorporated onto the test apparatus to automatically aspirate the test tubes in the linkage on an individual basis in sequential order. Mixing means for mixing the test tubes before aspiration are also provided on the conveyor module.

The test apparatus is thus rendered capable of operating on automatic closed tube samples when the aspiration and conveyor modules are in operation. Computer controls which control the operation of the conveyor module and the aspiration module are interconnected with computer controls that control the operation of the test apparatus.

Whether the automatic sampling system is modular or nonmodular, the feeding of test tubes to an aspiration station in continuous fashion and the mixing of selected test tubes as a group separate and apart from other test tubes in the linkage, without affecting the integrity of the linkage, enables the automatic sampler to operate without interruption until all test tubes in the linkage have been tested.

The invention accordingly comprises the constructions and method hereinafter described, the scope of the invention being indicated in the claims.

DESCRIPTION OF THE DRAWINGS

In the accompanying drawings,

FIG. 5 is an enlarged elevational view of two adjacent test tube holders in the linkage;

FIG. 6 is a view taken along the line 6—6 of FIG. 5;

FIG. 7 is a front elevational view of the conveyor module;

FIG. 8 is a top plan view of the conveyor module;

FIG. 9 is a fragmentary perspective view of a mix table;

FIG. 10 is a simplified end view of the linkage stacked in a fan-fold or Z-fold arrangement;

FIG. 11 is a fragmentary side elevational view of the mix table in a transport position;

FIG. 12 is a fragmentary side elevational view of the mix table in a stat position, the cover of the mix table being opened;

FIG. 13 is a fragmentary side elevational view of the mix table in the stat position with the cover closed;

FIG. 24 is a detailed schematic diagram of the electrical functions during mixing;

FIG. 25 is a simplified schematic diagram of the electrical functions during transport of a test tube to an aspiration position; and FIG. 26 is a detailed schematic diagram of the process of aspiration.

Corresponding reference characters indicate corresponding parts throughout the several views of the drawings.

DETAILED DESCRIPTION OF THE INVENTION

Figure 1:
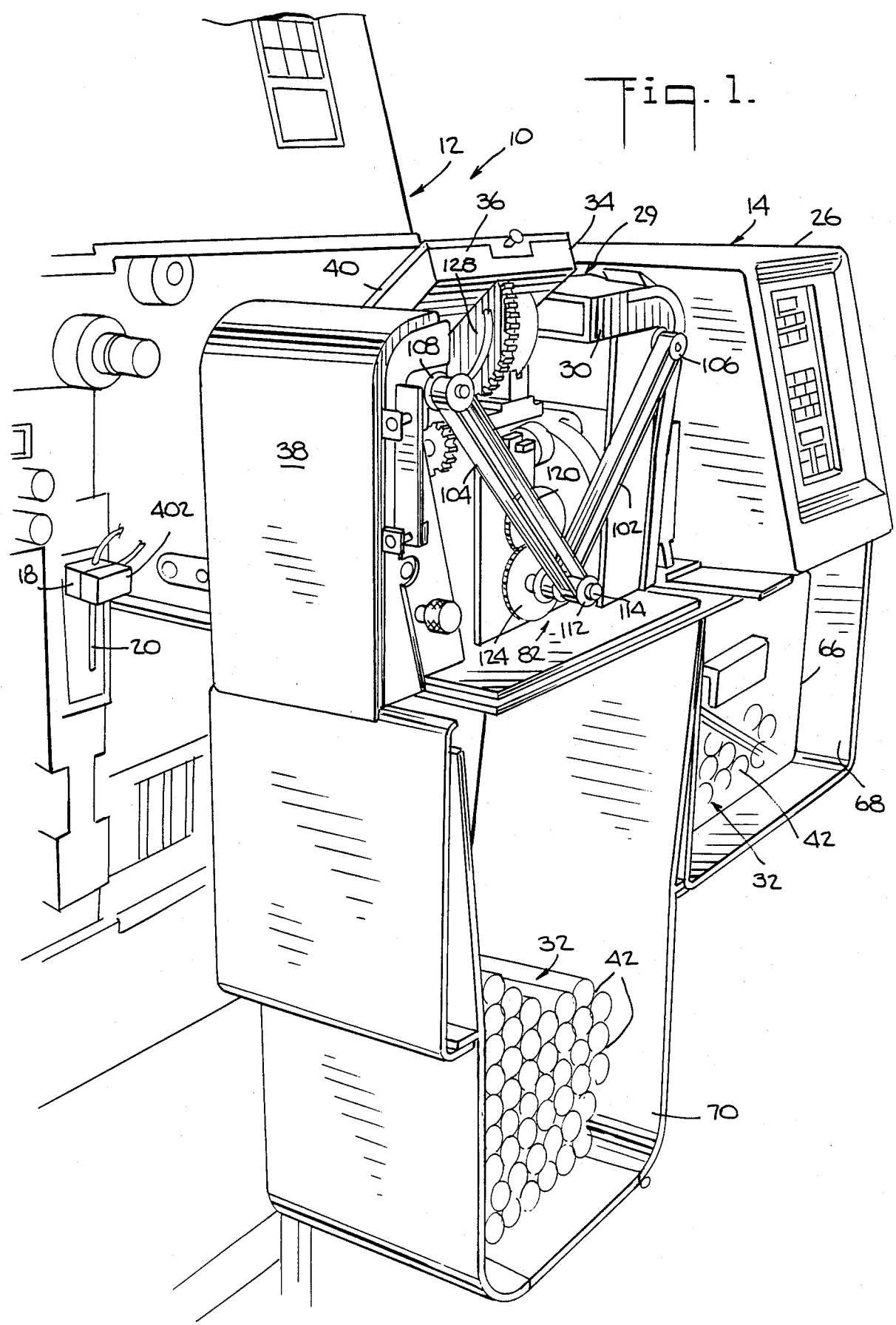
FIG. 1 is a perspective view of an automatic sampling system incorporating one embodiment of the invention.

An automatic sampling system (hereinafter referred to as sampler) incorporating one embodiment of the invention is generally indicated by the reference number 10 in FIG. 1.

The sampler 10 includes a test apparatus 12 for performing a plurality of tests on a sample of fluid such as blood, to determine specific characteristics of the blood. The sampler 10 further includes a conveyor module 14 pivotally and detachably secured to the test apparatus 12, and an aspiration module 16 (FIG. 2) also detachably secured to the test apparatus 12.

The test apparatus 12 is a self contained fully operational analyzer, but normally requires manual feeding of open tube samples to an aspiration head 18 having a depending aspiration needle 20. The aspiration module 16 supersedes operation of the aspiration head 18 when a sample port selector switch 402 (FIG. 19) is set to select the automatic mode of operation and the conveyor module 14 is in the position of FIG. 1.

The apparatus 12 further includes a reagent station 22 (FIG. 2) with reagent containers 24 that are used in the chemical analyses that are the bases for many of the tests performed in the apparatus 12. Further details of the apparatus 12 and the tests performed therein may be found in U.S. Pat. Nos. 3,740,143; 3,741,875; 4,575,490; 4,487,700; and U.S. patent application Ser. No. 431,639 filed Sept. 30, 1982; the disclosures of which are incorporated herein by reference.

Figure 2:
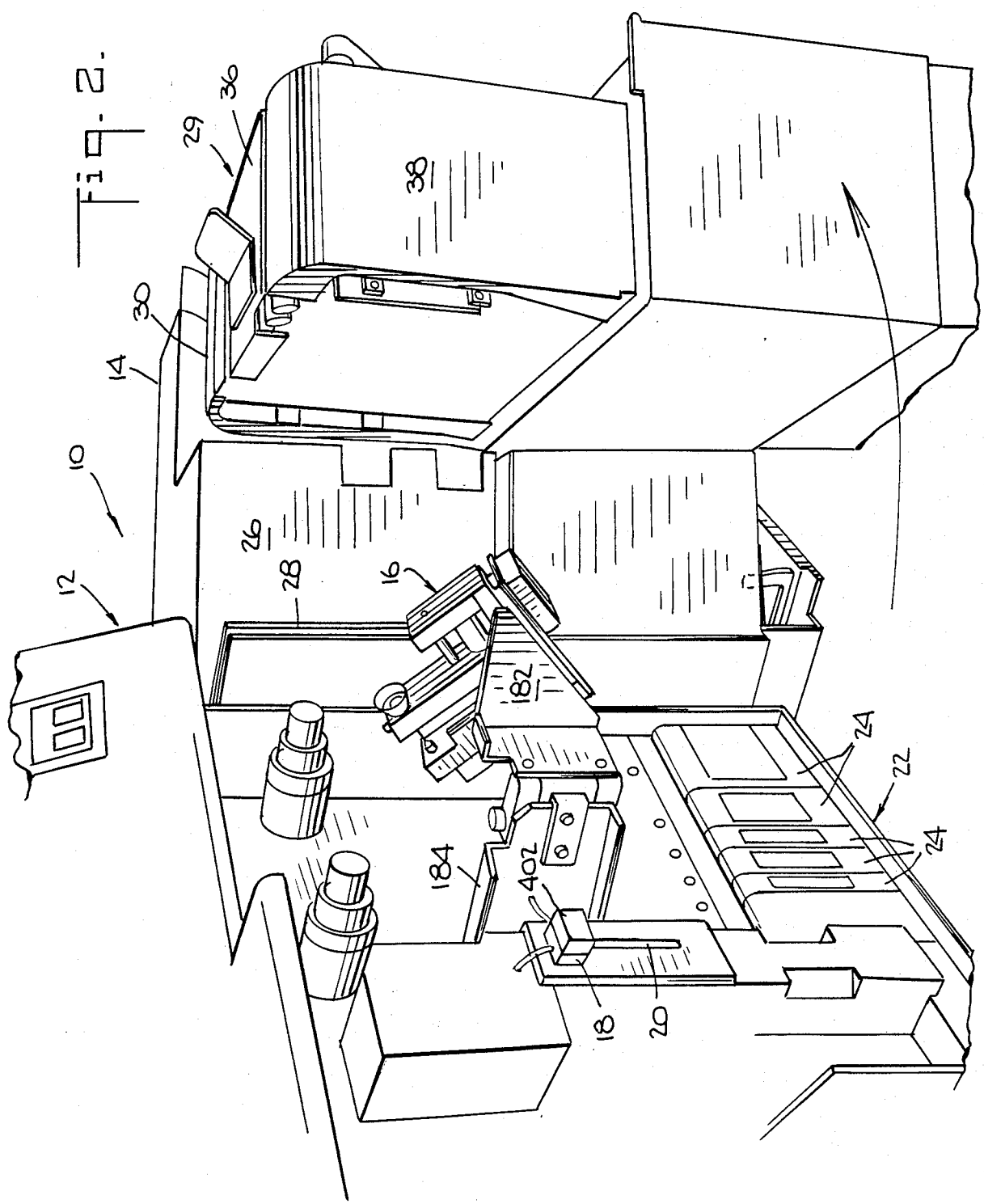
FIG. 2 is a perspective view thereof showing a conveyor module thereof pivoted away from a test apparatus thereof.
Figure 17:
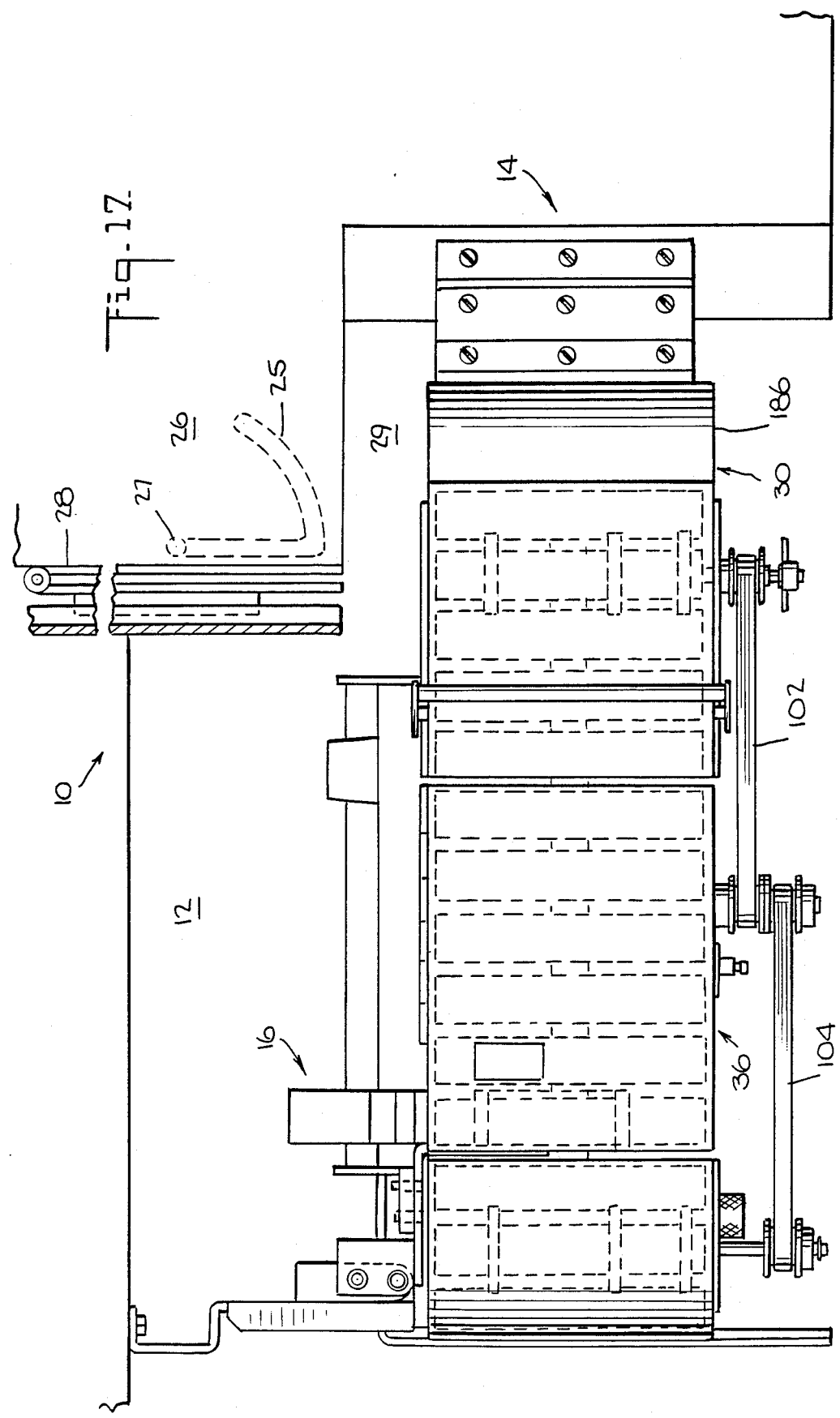
FIG. 17 is a top plan view of the conveyor module operationally joined to the test apparatus.
Figure 18:
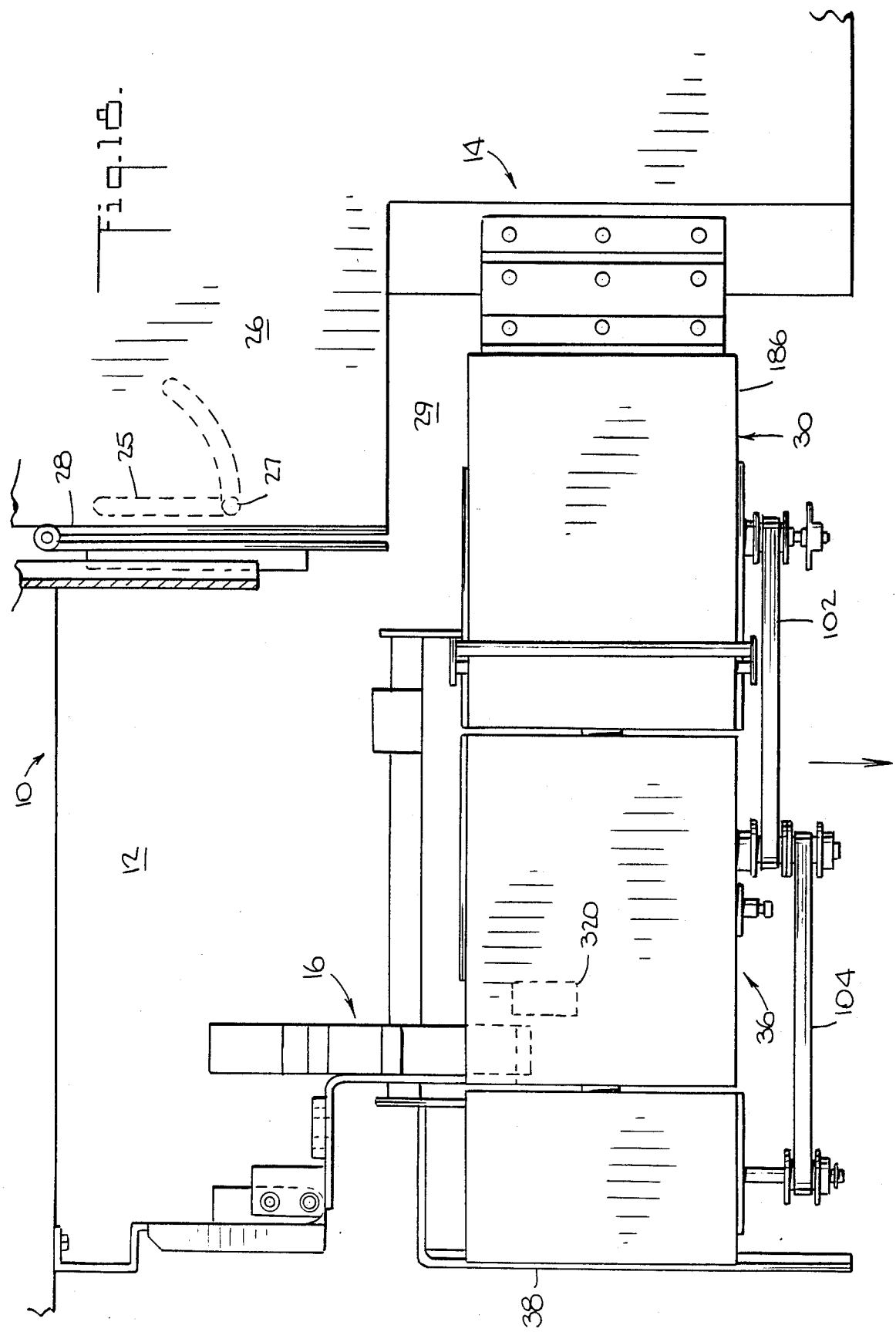
FIG. 18 is a view similar to FIG. 17 showing the conveyor module partially separated from the test apparatus.

Referring to FIGS. 2 and 17, the conveyor module 14 includes a computer housing 26 that is pivotally joined, as by a hinge member 28 (FIG. 17), to the test apparatus 12 for movement in and out of proximity with the aspiration module 16. If desired, the computer housing 26 can be provided as a separate module. Referring to FIGS. 17 and 18, a guide slot 25 and an engaging guide pin 27 permit linear and radial displacement of the conveyor module 14 away from the test apparatus 12, for service access to the test apparatus 12 and the reagents 24.

Figure 4:
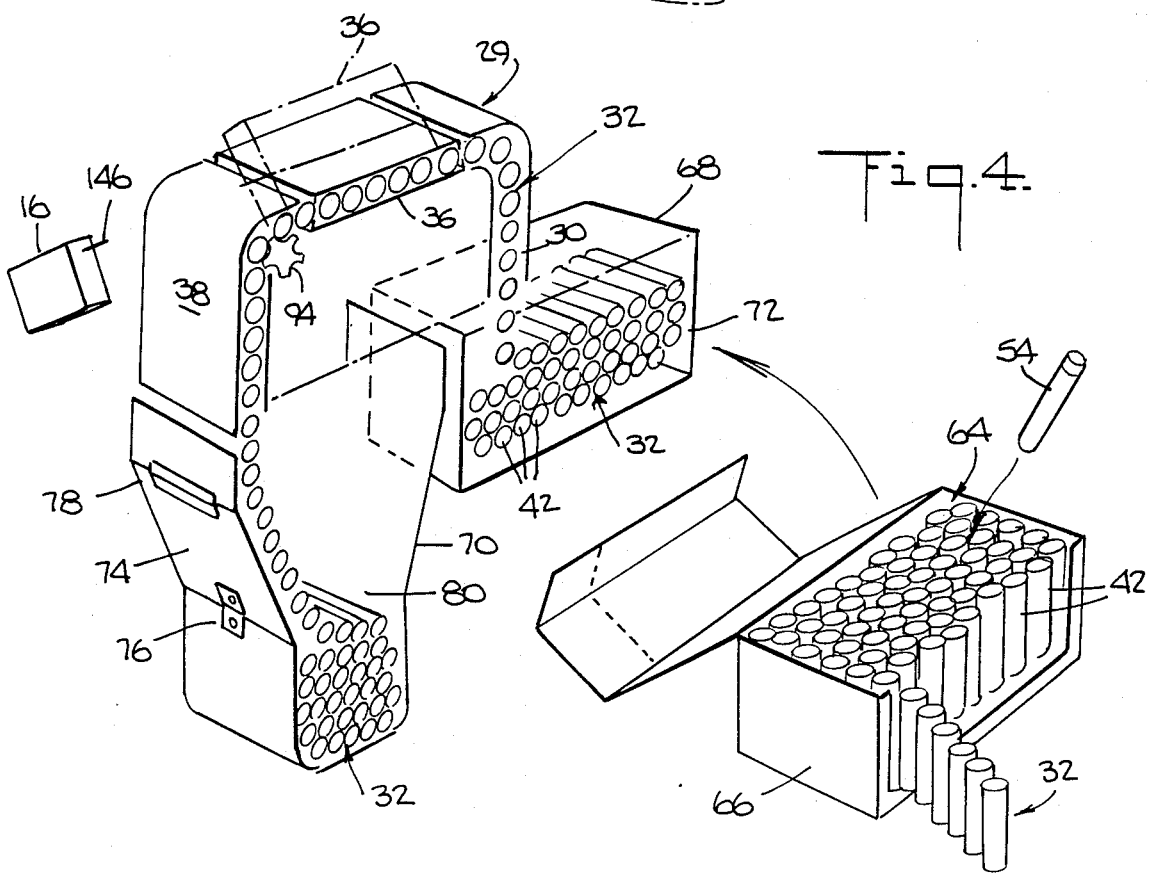
FIG. 4 is a simplified schematic perspective view of the conveyor module.

Referring to FIGS. 1, 4 and 7, the conveyor module 14 also includes linkage guide means 29 for guiding the transportation of a linkage 32. The linkage guide means 29 includes an input linkage guide 30 which leads to an entrance portion 34 (FIG. 7) of a mix table 36, and an output linkage guide 38 which leads away from an exit portion 40 of the mix table 36.

Figure 3:
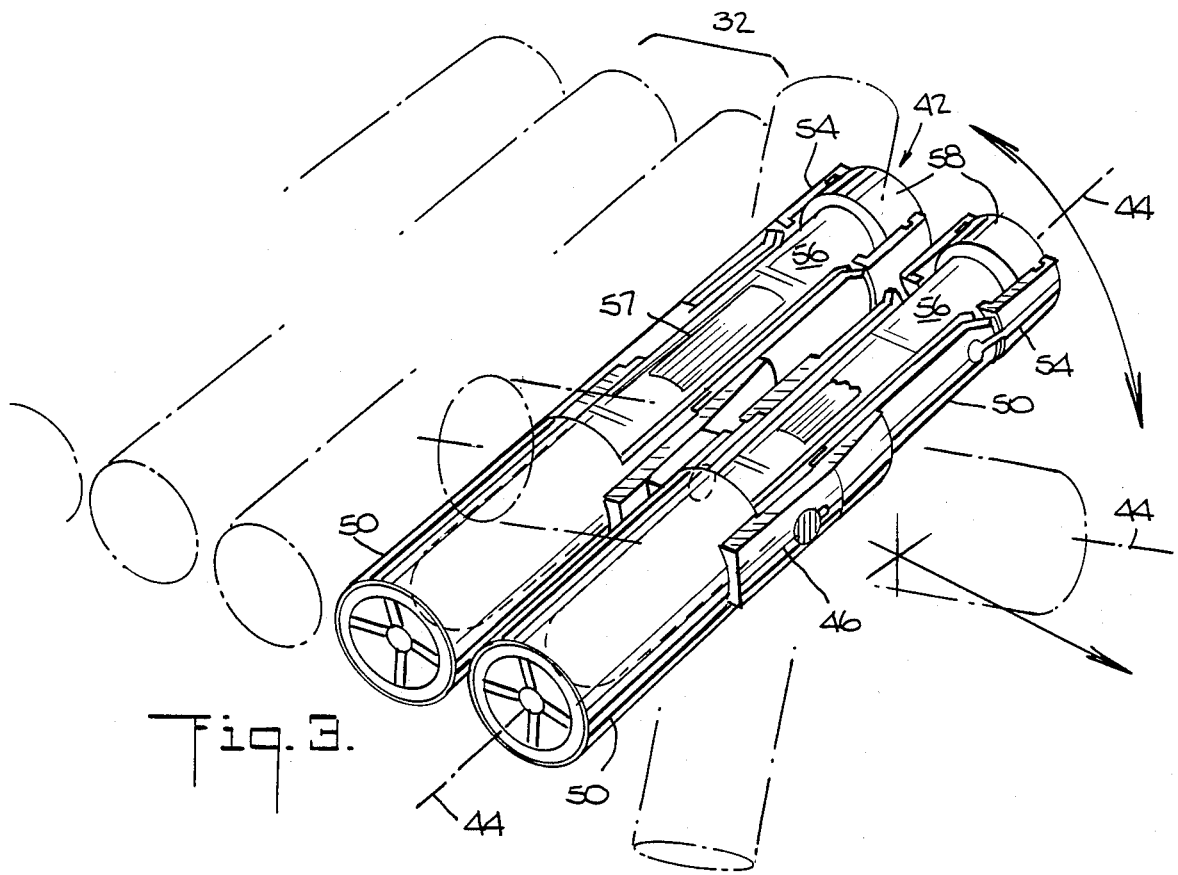
FIG. 3 is a perspective view of test tube holders joined together to form a linkage transported by the conveyor module.

Referring to FIGS. 3, 5 and 6, the linkage 32 comprises a plurality of test tube holders 42 elongated along an axis 44 and detachably joined together at complementary shaped latch members 46 and 48. The latch members 46 and 48 form a pivotal joint that permits bi-directional tilting movement between adjacent test tube holders 42 such that the longitudinal axis 44 of one test tube holder is inclinable with respect to the longitudinal axis 44 of an adjacent test tube holder 42, as shown in FIG. 3.

Each test tube holder 42 comprises an elongated tubular member 50 which incorporates the latch member 46 and a collar-shaped pivot member 52 supported on the tubular member 50 for radial movement with respect to the longitudinal axis 44 of the test tube holder 42.

The terms "axial" and "radial" as used herein relate to the longitudinal axis 44 as a frame of reference. Thus, unless otherwise indicated, "axial" refers to a distance or direction parallel to the longitudinal axis 44 and "radial" refers to a distance, direction or location that has a center on the longitudinal axis 44.

The pivot member 52 incorporates the latch member 48. Thus the pivot member 52 along with the latch members 46 and 48 constitute latching means for detachably joining adjacent test tube holders 42 together. The latching means 52, 46 and 48 permit bi-directional pivotal movement between adjacent test tube holders 42 (FIG. 3) such that the longitudinal axis 44 of one test tube holder is an axis of rotation for an adjacent test tube holder. A 270° bi-directional range of radial- pivotal movement is obtainable under this arrangement and the linkage 32 is thus afforded sufficient flexibility to be stacked in the fan-fold or Z-fold arrangement of FIG. 10.

The test tube holder 42 further includes an adapter member 54 that is detachably receivable in the elongated tubular member 50 in a manner whereby the collar-shaped pivot member 52 embraces the adapter member 54. The adapter member 54 has sufficient clearance from the pivot member 52 to permit relative radial movement therebetween.

A test tube 56, which can be of the closed-tube type sold under the trade name Vacutainer by Becton Dickinson, is inserted in the adapter member 54, before or after the adapter member 54 has been positioned in the elongated tubular member 50. The test tube 56 is normally sealed with a stopper 58.

The adapter member 54 is interchangeable in the elongated tubular member 50 with other adapter members that accommodate test tubes of different size such as the adapter member 60 which accommodates a test tube 62 as shown in FIG. 6.

If desired, an annular retaining ring 64 (FIG. 5) can be inserted in a radial groove 65 of the adapter member 60 to enhance retention of the test tube 64 or any other size test tube in its respective adapter member, especially if the test tube has been previously opened.

A more complete description of the structure and operation of the test tube holder 42 is contained in the copending application entitled Test Tube Holder filed simultaneously with this application, the disclosure of which is incorporated herein by reference.

The engagement of the latch members 46 and 48 of adjacent test tube holders 42 permits development of the linkage 32 to any selected length based on the number of test tube holders 42 joined together in the linkage 32. Additional linkages 32 can be attached to a linkage 32 that is already in the input compartment 68. Such additions can be made as desired. Thus, the linkage 32 of test tube holders 42 can be of theoretically unlimited length.

As shown schematically in FIG. 4, the linkage 32, when developed to a predetermined length, can be prepackaged in a cassette or container 66 for installation in an input compartment 68 that communicates with the input linkage guide 30. Similarly, an output compartment 70 receives and stores the linkage 32 exiting from the output linkage guide 38.

When the linkage 32 is of a length which exceeds the capacity of the input and output compartments 68 and 70, an input door 72, shown schematically on the input compartment 68 of FIG. 4, is opened to permit the incoming linkage 32 to pass through the input door 72 into the input compartment 68.

An output door 74, shown schematically on the output compartment 70 in FIG. 4, can also be opened via the latch 76 and the hinge 78 to permit the exiting linkage 32 to bypass the storage space 80 of the output compartment 70 and move into a larger receiving container (not shown).

Figure 19:
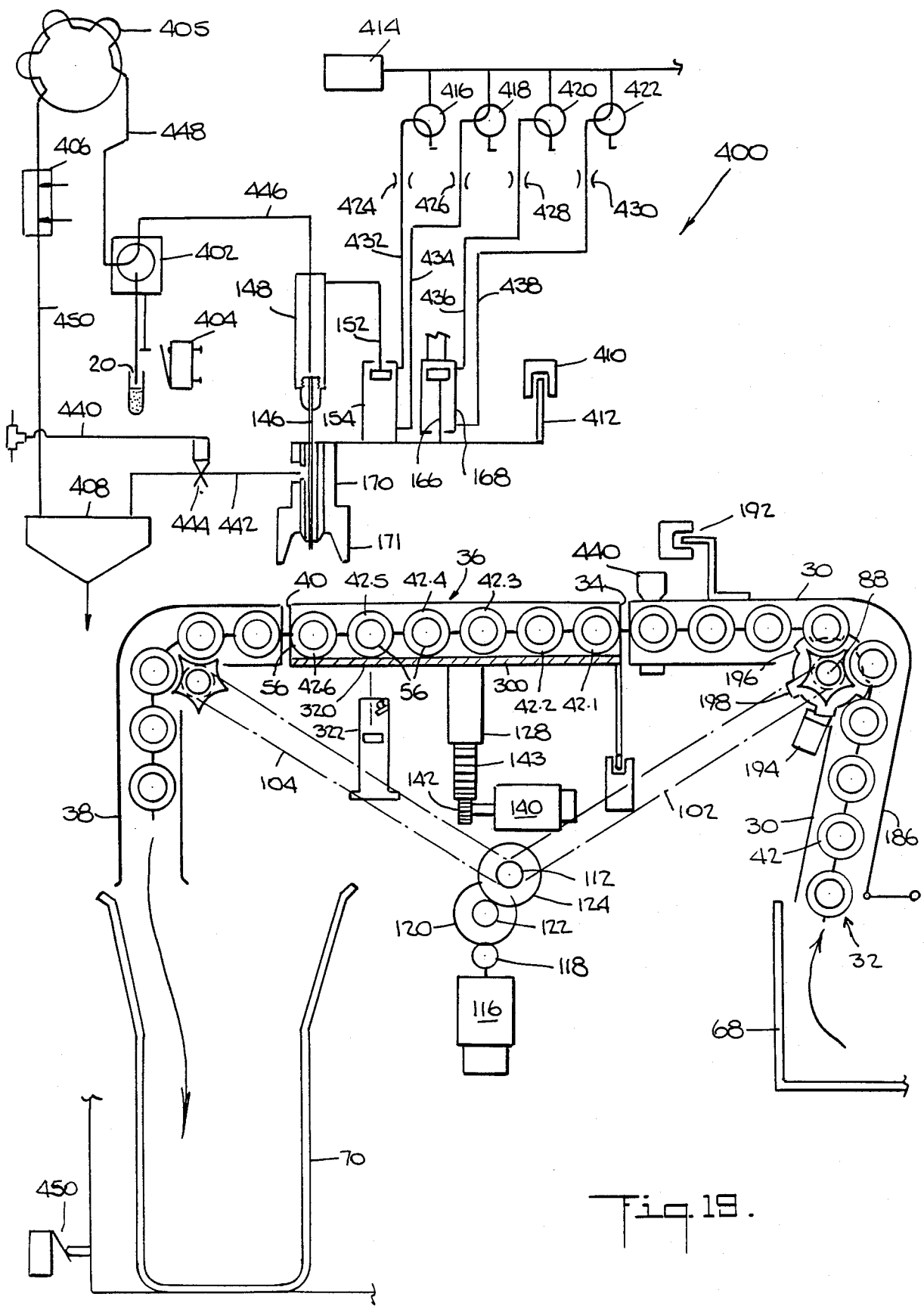
FIG. 19 is a simplified schematic view of the conveyor module and the pneumatic circuit for operating the aspiration module.

Another option is to provide removable input and output bins 68 and 70 as shown schematically in FIG. 19. Thus the input and output compartments 68 and 70 can be entirely removed from the conveyor module 14 when linkages 32 of unlimited length are being used, to provide an unconfined space for incoming and exiting linkage.

Referring to FIGS. 7, 8 and 9, drive means for engaging the test tube holders 42 of the linkage 32 to move the linkage 32 through the input and output linkage guides 30 and 38 is generally indicated by the reference number 82. The drive means 82 includes a pair of input sprockets 84 and 86 (FIGS. 7 and 8) fixed to a shaft 88 rotatably mounted near a bend 90 in the incoming linkage guide 30.

Similarly, a pair of output sprockets 92 and 94 are fixed to an output shaft 96 located near a bend 98 in the outgoing linkage guide 38. Cusp portions 100 of the sprockets 84, 86, 92 and 94 are sized to engage the periphery of any of the test tube holders 42 in the linkage 32 in the manner shown in FIG. 9.

The input and output sprocket shafts 88 and 96 are belt driven by respective toothed belts 102 and 104 which engage correspondingly toothed driven members 106 and 108 fixed to the respective input and output sprocket shafts 88 and 96.

The toothed belts 102 and 104 also engage respective toothed driving hubs 110 and 112 respectively fixed to a drive shaft 114. The drive shaft 114 is powered by a transport motor 116 through a gear train which includes a motor pinion 118, an idler gear 120, an idler pinion 122 and a driven gear 124 fixed to the drive shaft 114. Under this arrangement, movement of the transport motor 116 causes movement of the input sprockets 84, 86 and the output sprockets 92, 94. A bearing housing 125, provided at an end of the drive shaft 114, is supported on a support plate 127 with the transport motor 116.

Referring to FIGS. 7, 9 and 11, mixing means for separately tilting a group of test tube holders 42 in the linkage 32, in bi-directional fashion, is generally indicated by the reference number 126 and includes the mixing table 36. The mixing table 36 comprises a support section 300 of predetermined width for supporting a predetermined number of test tube holders. In the preferred embodiment, the mixing table 36 spans six test tube holders 42 in the linkage 32 indicated by the reference numbers 42.1, 42.2, 42.3, 42.4, 42.5, and 42.6.

The mixing table 36 further includes a rear wall 302 extending from the entrance portion 34 to the exit portion 40. A front wall 304 extends from the entrance portion 34 to an access opening 306. The access opening 306 spans two test tube holders 42.5 and 42.6, the test tube holder 42.6 being in a position referred to as the sampling or aspiration position.

A cover member 308 is pivoted at 310 to the front wall 304 and includes a cut out 312 which borders the access opening 306. The cover member 308 also includes a handle 314 and a latch member 316 (FIG. 11) which engages a latch member 318 on the rear wall 302 to hold the cover member 308 in a closed position. A reader opening 320 (FIG. 19) is formed in the support section 300 in alignment with the test tube holder 42.5 and in alignment with an ID reader 322 (FIG. 7) supported on a base piece 324.

Referring to FIGS. 7 and 11, the mixing means 126 further includes a generally semicircular sector gear 128 joined to an underside of the support section 300. A radial guide slot 132 is formed in the sector gear 128 and is radial with respect to a center 129 of the sector gear 128 which is coincident with an axis passing through the centers of the latch members 46 and 48 of all test tube holders 42 on the mixing table 36. The mixing action of the mixing table 36 thus provides pivotal movement of the test tube holders 42.1, 42.2, 42.3, 42.4, 42.5 and 42.6 about a substantially diametrical axis of the test tubes 56 in the test tube holders 42.

A pair of spaced support rollers 134 and 136 extend into the radial guide slot 132 from a support plate 138. The support rollers 134 and 136 are sized to permit bi-directional pivotal movement of the sector gear 128 about its center with respect to the support rollers 134 and 136. Such bi-directional movement is accomplished via a mix motor 140 (FIG. 7) supported at the support plate 138. A motor pinion 142 on the mix motor 140 engages an idler gear 143 that engages the sector gear 128. A mix sensor plate 144 depends from the support section 130 in alignment with a sensor 145, supported on the plate 138.

Referring to FIGS. 11, 12 and 13, the aspiration module 16 is provided at a predetermined sampling station on the test apparatus 12 for cooperation with the conveyor module 14. The aspiration module 16 includes an aspiration needle 146 provided on a mounting block 148 that is slidably supported on a shaft 150. The mounting block 148 is also affixed to the piston rod 152 (FIG. 16) of a pneumatic cylinder 154 having fluid line connectors 156 and 158.

A yoke member 160 is affixed to the pneumatic cylinder 154 next to the fluid line connector 156. The yoke member 160 is mounted to a slider bracket 162 slidably mounted on the shaft 150. The slider bracket 16 is affixed to a mounting collar 164 mounted on a piston shaft 166 of a pneumatic cylinder 168. The pneumatic cylinder 154 is thus slidably mounted on the shaft 150, the slidable movement of the cylinder 154 being controlled by the pneumatic cylinder 168. The pneumatic cylinder 168 also includes fluid line connectors (not shown) similar to the fluid line connectors 156 and 158 of the pneumatic cylinder 154.

A centering frame 170 is slidably supported on the shaft 150 and normally maintained in a spaced relationship from the mounting block 148 by a spring 172. The centering frame includes a centering collar 171 preferably formed of plastic for centering the stopper 58 of a test tube 56 just before the aspiration needle 146 penetrates the stopper 58. The centering frame 170 includes a leg portion 174 that extends parallel with the shaft 150 and joins the slider bracket 162. The centering frame 170 is thus moveable in unison with the pneumatic cylinder 154 by the pneumatic cylinder 168. A spring 176 is disposed between the leg portion 174 and an end wall 178 of a support member 180. The support member 180 is joined to a support flange 182 (FIG. 2) that is pivotally joined to a support beam 184.

In operation of the sampler 10, a linkage 32 of test tube holders 42 of any preselected length is placed in the input compartment 68. A lead end of the linkage 32 (not shown) is fed into the input linkage guide 30. An input cover 186 (FIG. 7) on the input linkage guide 30 facilitates access to the linkage 32 as it is being fed through the input linkage guide 30. The linkage 32 is manually inserted into the linkage guide 30 with one of the test tube holders 42 engaging a cusp portion 100 of the input sprockets 84 and 86. The input cover 186 is then closed thereby actuating an input cover sensor 192 (FIG. 19) which enables the conveyor system to operate.

A hold-down member 188 (FIG. 7) is biased by a spring member 190 against a test tube holder 42 located at the input sprocket members 84, 86 as the test tube holder 42 starts to move horizontally with respect to FIG. 7 toward the mixing table 36. The hold-down member 188 helps assure accurate control of the test tube holder positions on the mixing table 36.

The transport motor 116 drives the gears 118, 120, 122 and 124 to power the toothed belt 102 to drive the linkage 32 from the input linkage guide 30 onto the mixing table 36.

During the mix cycle, the mixing motor 140 drives the motor pinion 142 in a first direction a predetermined amount to rotate the sector gear 128 approximately 45° in one direction. The mixing motor 140 then reverses direction to cause to sector gear 128 to likewise reverse direction and pivot the mixing table 36 approximately 45° in the reverse direction.

The pivot connection between adjacent test tube holders 42 in the linkage 32 permits relative tilting movement therebetween as shown in FIG. 3. It should be noted that one test tube holder 42 alone can be tilted with respect to a series of other test tube holders 42 linked together, or several test tube holders 42 can be tilted in unison with respect to several other test tube holders 42, all of which are connected together in one linkage.

The relative tilting capability of test tube holders 42 in the linkage 32 permits the mixing table 36 to mix the group of test tube holders 42.1, 42.2, 42.3, 42.4, 42.5, and 42.6 as a group separate and apart from other test tube holders in the input linkage guide 30 and in the output linkage guide 38. The mixing operation takes place without affecting the integrity of the connection between all test tube holders 42 in the linkage 32.

Preferably there are six reversals of direction of the mixing table 36 for each mix cycle. The speed of movement of the mixing table is predetermined based on the type of fluid being tested. Mixing usually occurs when an air bubble in the sealed test tube 56 rises in the fluid with each tilt of the mixing table 36. The motor speed profile of the mixing table 36 provides rapid acceleration to capture an air bubble (not shown) in the test tubes 56 momentarily at one end, and then permit the bubble to rise to the opposite end before the mixing table 36 is again tilted.

Only when the mixing table 36 is in the horizontal position as shown in FIG. 11, will the transport motor 116 operate to transport the linkage 32 through the input and output linkage guides. Thus, the horizontal position of the mixing table 36 as shown in FIG. 11 is known as the transport position.

When the mixing table 36 is pivoted approximately 45° toward the toothed belts 102 and 104, as shown in FIGS. 12 and 13, it is located in the stat position. Manual interchange of a test tube 56 in the position next to the sampling position can be accomplished when the mixing table 36 is in the stat position. Thus the cover 308 is placed in the open position of FIG. 12 by disengaging the latch 316 from the latch detent 318.

Referring to FIG. 9, the adapter member 54 of the test tube holder 42.5 is removed without disengaging the connection with the adjacent test tube holders 42.4 and 42.6. A replacement adapter member and test tube can then be received in the test tube holder 42.5. This type of interchange of test tubes is usually made when another test tube has a sample that requires immediate testing.

Figure 14:
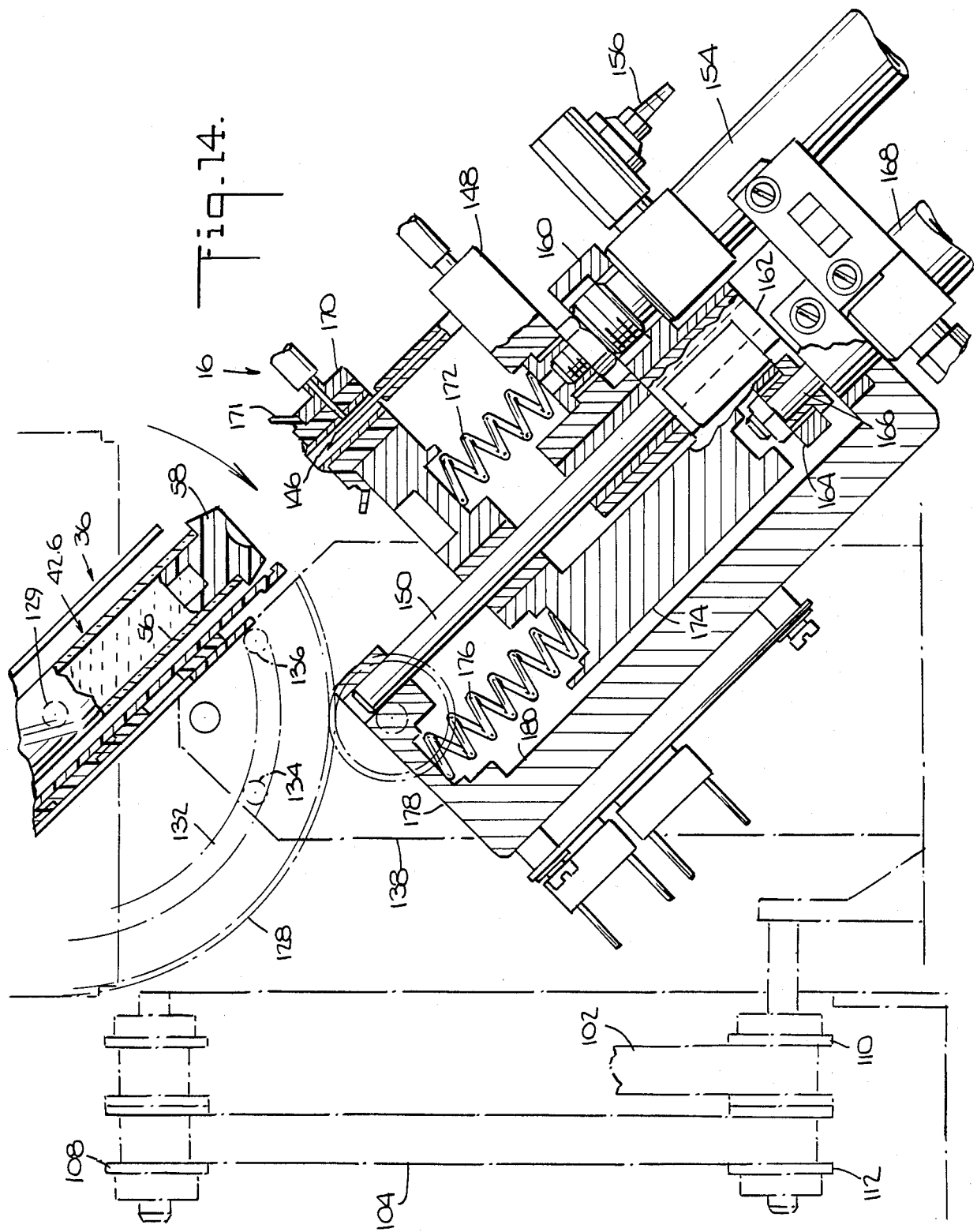
FIG. 14 is a side sectional view showing the mix table in the aspirate position with respect to the aspiration module when the aspirate needle is in a retracted position.

When the mixing table 36 is pivoted 45° toward the aspiration module 16 as shown in FIG. 14, it is in the home position or aspiration position. Thus, the test tube holder 42.6 which is in the sampling position on the mixing table 36 as shown in FIG. 9, aligns with the aspiration needle 146.

A pneumatic circuit for controlling the operation of the aspiration module 16 is generally indicated by the reference number 400 in FIG. 19. The pneumatic circuit 400 includes a schematic representation of the centering frame 170 and the centering collar 171, the aspiration needle 146, the mounting block 148, and the pneumatic cylinders 154 and 168. The pneumatic circuit 140 also includes a sample port selector valve 402, a microswitch 404 and a shear valve 405 connected to a conductivity detector 406 which leads to a waste bin 408.

A needle clear sensor 410 cooperates with a needle clear vane 412. An air supply 414 feeds air through the lines 432, 434, 436 and 438 which respectively include solenoid air escape valves 416, 418, 420, and 422, and flow controllers 424, 426, 428, and 430.

A tube sensor 440 is provided on the input linkage guide 30 just before the entrance portion 34 of the mixing table 36.

The pneumatic circuit 400 is operational when the selector valve 402 is turned to a predetermined position corresponding to automatic operation, wherein test tubes 56 on the linkage 32 are automatically aspirated. The switch 402 also has a position which enables the apparatus 12 to operate on manually introduced open test tubes which are aspirated through the aspiration probe 20. When the valve 402 is in the automatic select position, the microswitch 404 signals the computer 622 (FIG. 17) to operate in the automatic mode.

The tube sensor 440 senses the presence of test tube holders 42 in the linkage 32 which contain test tubes 56 with fluid to be tested. It should be noted that some test tube holders 42 may not contain a test tube 56 for one reason or another. Once the sensor 440 has sensed the presence of a test tube with fluid in a test tube holder 42 that moves onto the mixing table 36, it causes the mixing operation to take place.

When the test tube containing fluid reaches the sampling position, which is six positions away from the sensor 440, and is mixed in the sampling position, the aspiration process will begin. Thus, the mixing cycle terminates with the mixing table 36 in the aspiration position as shown in FIG. 14.

Figure 15:
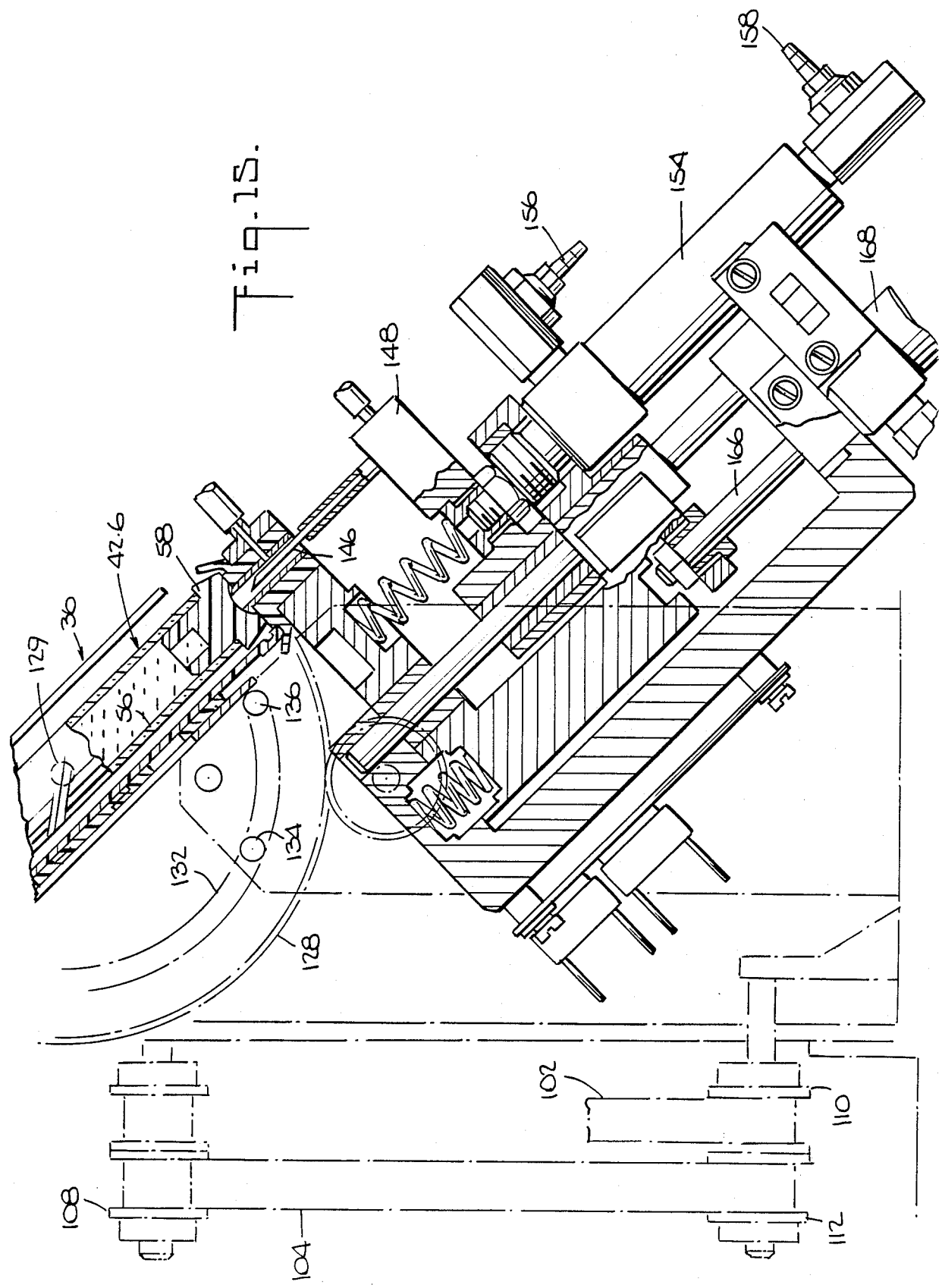
FIG. 15 is a view similar to FIG. 14 which shows the aspiration module centering a test tube on the mix table before aspiration.

The centering collar 171 and the needle mount 148 are moved from the position of FIG. 14 to the position of FIG. 15 when air is permitted to enter line 436 of the cylinder 168. The centering collar 171 thus engages and centers the stopper 58 of the test tube holder 42.6 before the needle 146 penetrates the stopper.

Figure 16:
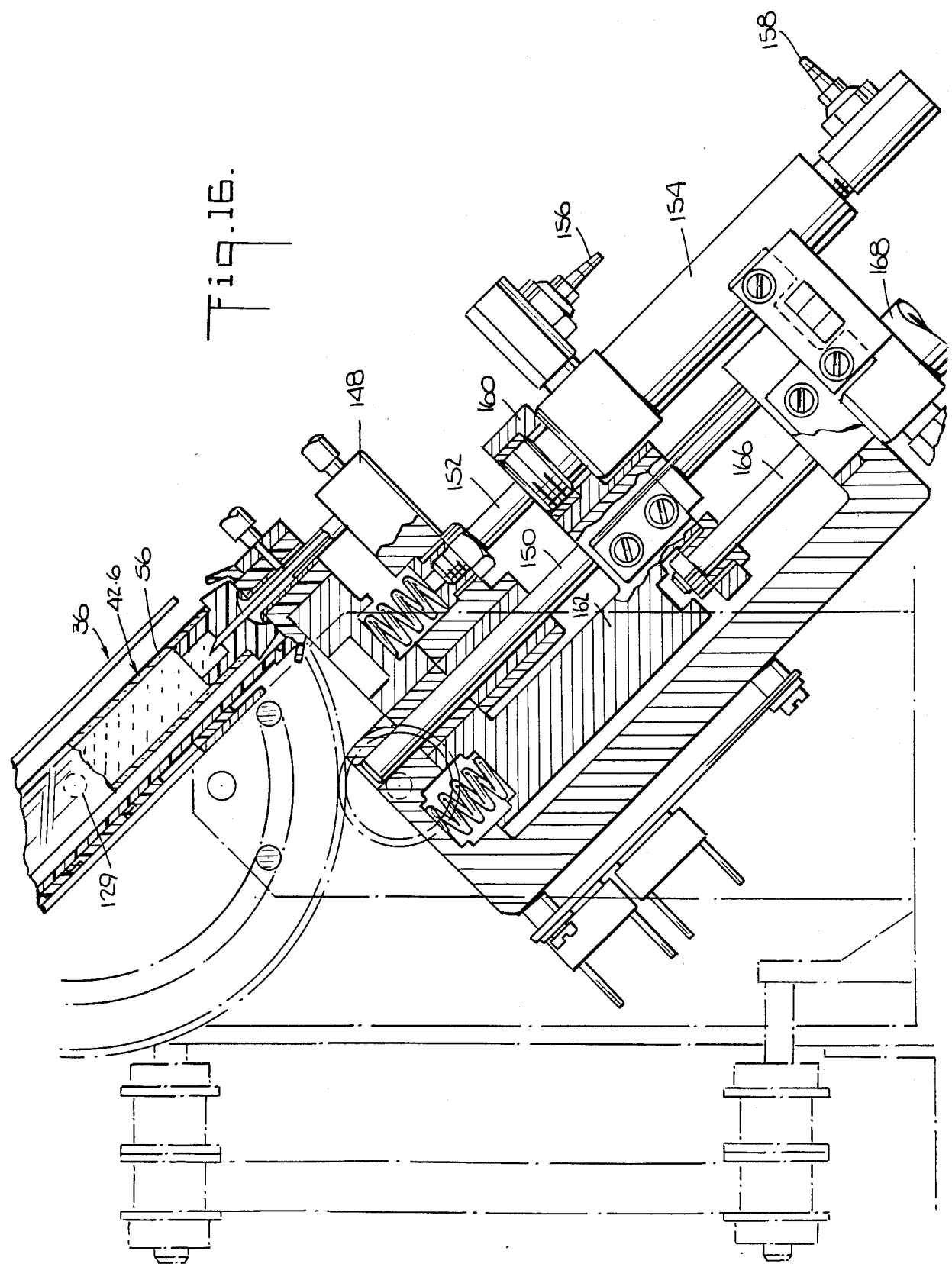
FIG. 16 is a view similar to FIG. 15 which shows the aspiration module withdrawing fluid from a test tube on the mix table.

After the stopper 58 has been centered by the centering collar 171, air enters line 432 of the pneumatic cylinder 154 to cause the piston rod 152 to move the mounting block 148 toward the stopper 58 in the manner shown in FIG. 16. The needle 146 thus penetrates the stopper 58 to withdraw fluid from the test tube 56 of the test tube holder 42.6.

Fluid withdrawn from the test tube 56 by the needle 146 passes through the line 446, through the valve 402 and the line 448 to the shear valve 405 and into the conductivity sensor 406 which signals the needle 146 to stop aspirating. The air escape valve 416 opens to permit air to escape through the line 432. Air is admitted into the cylinder 154 through the line 434 to retract the needle mounting block 148 and the needle 146 from the stopper 58.

The collar 171 remains in the centering position around the needle stopper 58 while the needle 146 is being withdrawn to the position of FIG. 15. The air escape valve 420 opens to permit air to escape from the cylinder 168 through the line 436. Air is next admitted through the line 438 into the cylinder 168 to cause the piston rod 166 to retract the centering frame 170 and the centering collar 171 from the position of FIG. 15 to the position of FIG. 14. A program provided in the computer 608 (FIG. 17) controls the timing of operation of the various valves in the pneumatic circuit 400. The springs 172 and 176 (FIGS. 14–16) also help restore the centering frame 170 and the mounting block 148 to their predetermined rest positions as shown in FIG. 14, although their primary function is to retract the needle and centering collar should primary air pressure be lost due to system failure or power failure.

With the needle 146 located in the collar 171, in the position of FIG. 14, a wash cycle takes place wherein wash fluid flows through the line 450, past the conductivity detector 406, into the shear valve 405, through the line 448, past the valve 402, into the line 446 to flush the inside and outside of the needle 146. The flushing liquid is drawn into the line 442 leading to the waste chamber 408. Further details of the wash cycle are contained in U.S. Pat. Application Ser. No. 771,895 filed Sept. 3, 1985, the disclosure of which is incorporated herein by reference.

When the collar 171 is retracted from the needle stopper 58, the vane 412 is in a position corresponding to the needle clear position. The needle clear information is sensed by the needle clear sensor 410 and the mixing table 36 is pivoted from the position shown in FIG. 14 to the transport position of FIG. 11. The transport position of the mixing table allows the linkage 32 to move an additional step equal to the pitch between the test tube holders 42. Thus the test tube holder 42.5 is moved into the sampling position previously occupied by the test tube holder 42.6.

When the test tube holder 42.5 is aligned with the ID reader 322 as shown in FIG. 19, a label 57 (FIG. 3) on the test tube 56 is read to identify the particular test tube sample. Standard ID codes such as a bar code can be provided on the test tube labels 57 before the test tubes are loaded into their test tube holders. The test tube held by the test tube holder 42.5 is thus fully identified by the computer 608 (FIG. 20) before the test tube holder 42.5 moves into the sampling position. The mix cycle is then repeated, followed by the aspiration cycle and again by a transport cycle.

If the sensor 440 does not detect a test tube in an initial test tube holder when the linkage 32 is first being loaded into the input linkage guide 30, there will be no mixing by the mixing table 36 when such test tube holder moves onto the mix table. However, as soon as the sensor 440 first senses a test tube 56 with fluid in a test tube holder 42, the mixing table 36 will go through a mix cycle.

The mix cycle occurs for each indexed movement of the fluid containing test tube holder on the mix table 36 until it reaches the sampling position, regardless of the filled or empty condition of test tube holders which follow the initial fluid containing test tube holder. Thus in the embodiment shown herein, a test tube holder containing a test tube with fluid will go through six mixing sequences on the mixing table 36, even if five empty test tubes follow. The sampler 10 provides a normal mixing operation for each indexed movement of the linkage 32 if every sixth test tube holder 42 in the linkage 32 is provided with a test tube having fluid therein.

Indexed movement of the linkage 32 a distance equal to the pitch between adjacent test tube holders 42 is governed by a transport sensor 194 (FIG. 19) positioned in proximity of a transport sensor vane 196 fixed to the input sprocket shaft 88. The transport sensor vane 196 has five lobes 198, 72° apart. The transport sensor 194 senses an exact 72° movement of the input sprocket shaft 88 and then stops the motor 116 from running. The motor 116 thus runs in accordance with the position of the transport sensor vane 196 as sensed by the transport sensor 194. The 72° rotation of the input sprocket is correlated to pitch between adjacent test tube holders 42 in the linkage 32. Under this arrangement there is accurate positioning of the test tube holders 42 in the sampling position, in alignment with the aspiration needle 146.

As previously noted, the movement of selected mechanical components in the sampler 10 are sensed by sensing devices. The positional location of such movements are ascertained and a further sequence of movements of further components of the sampler 10 is accomplished based on a computer program that controls all stages of operation of the sampler 10 including movement of the linkage 32, movement of the mixing table 36, the appropriate cessation of such movement, and the operation of the aspiration module 16.

Figure 20:
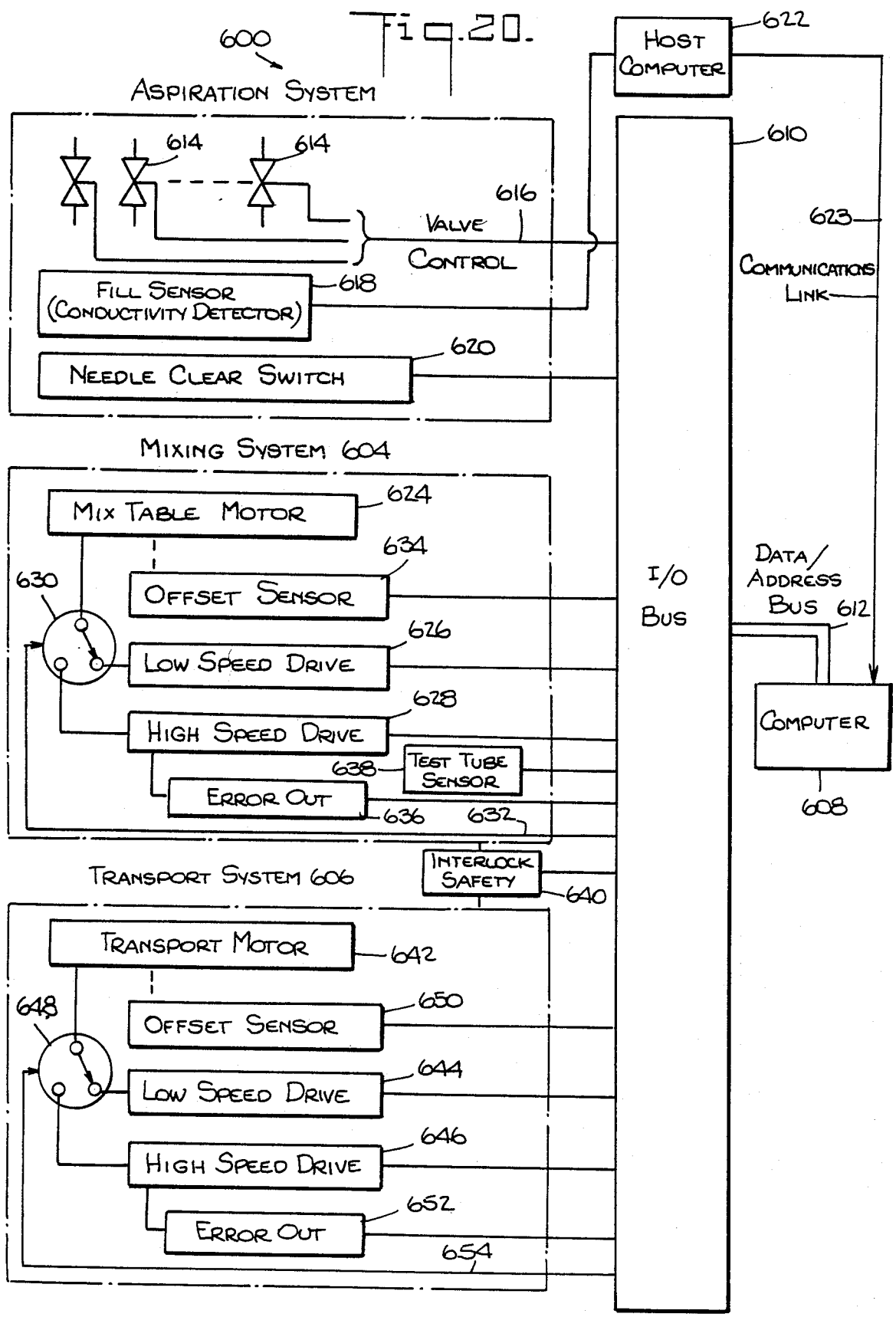
FIG. 20 is a simplified schematic diagram of the aspiration, mixing and transport processes.

A simplified schematic diagram of an electronic system 600 for operating the transport, mixing and aspiration functions of the automatic closed tube sampler is shown in FIG. 20. The system 600 comprises three smaller systems, namely, an aspiration system 602 for aspirating a test sample of fluid from each test tube, a mixing system 604 for controlling the mixing of test tubes containing samples of blood or other fluids, and a transport system 606 for transporting test tubes toward and away from the aspirator. The systems 602, 604 and 606 are operated under control of a computer 608, and are coupled to the computer 608 via a set of input/output (I/O) devices 610 and a data/address bus 612.

In the aspiration system 602, the valves 614 provide for pneumatic control of the advancement and retraction of the aspiration needle. The valves 614 are electrically activated by signals generated in the computer 608 and coupled via the I/O devices 610 and I/O lines 616 to the individual valves 614. The activation signals applied via the lines 616 are generated by the computer 608 in response to information provided by the aspiration system 602 to the computer 608. The information includes the presence of the test tube, the location of the aspiration needle, interlock status and whether a predetermined amount of fluid such as blood has been aspirated from a test tube.

A fill sensor 618 includes an electrical conductivity detector, operative in response to the presence of fluid in an aspirating container (not shown in FIG. 20). The fill sensor 618 applies a signal to the computer 608 through a host computer 622 of the test apparatus 12 via a communication link 623 to indicate when the predetermined amount of fluid has been aspirated. A needle clear switch 620 provides a switch closure to the I/O device 610 to indicate to the computer 608 that the aspiration needle (not shown in FIG. 20) has been fully withdrawn so as to clear mechanical elements of the mixing and transport systems 604 and 606, thereby permitting operation of the systems 604 and 606.

In the mixing system 604, the electric motor 624 which tilts the mixing table (not shown in FIG. 20) to provide for the mixing of fluid in the test tubes, is activated electrically by two electronic drives 626 and 628. The drive 626 is a low speed drive which is employed for accurately positioning the mix table in preparation for aspiration. The drive 628 is a high speed drive employed for tilting the table back and forth. The two drives 626 and 628 receive signals from the computer 608 via the I/O devices 610, and are selectively coupled via an electronic switching system 630 to the motor 624.

Operation of the electronic switching system 630 is controlled by the computer 608 via the I/O lines 632.

Both the drives 626 and 628 operate in a closed loop fashion. In the low speed drive 626, a loop error signal is provided by a sensor 634 mechanically coupled to the mixing table. The sensor 634 outputs an electric signal which indicates to the computer 608 the position of the table relative to a predetermined position. In the high speed drive 628, an error detector 636 outputs to the computer 608 a difference between a computer designated amount of motor shaft rotation and an actual value of motor shaft rotation. Also present in the mixing system 604 is a test tube sensor 638 which provides an indication to the computer 608 of whether a test tube is present in a specific slot or test tube holder of the transport conveyor. This information indicates to the computer 608 whether the mixing and/or aspiration functions are to be performed.

An interlock 640 is employed for the safety of personnel operating the system 600, and includes switches (not shown) on protective doors and paneling which enclose electrical and mechanical components of the delivery system. The interlock 640 signals the computer 608 of a hazard, such as an open door, so that the computer can respond by terminating mechanical movement.

In the transport system 606, an electric motor 642 is employed for advancing the conveyor (not shown in FIG. 20) for successively delivering test tubes to the mixing table and to the aspiration location. The transport motor 642 is also electrically operated by a low speed drive 644 and a high speed drive 646 which are selectively coupled via an electronic switch 648 to the transport motor 642. Both the drives 644 and 646 operate in a closed-loop fashion. A feedback of signal for the low speed drive 644 is provided by an offset sensor 650 which is mechanically coupled to the conveyor. The offset sensor 650 generates an electrical signal indicating an offset from a desired position of the conveyor, the electrical signal being applied via the I/O devices 610 to the computer 608.

In the high speed drive 646, an error detector 652 outputs the difference between a computer designated motor shaft rotation and an actual value of shaft rotation. The output signal of the detector 652 indicates to the computer 608 the error between a designated location of the conveyor and the actual location of the conveyor. The high speed drive 646 is employed to advance the conveyor to bring a test tube to the approximate location for aspiration, while the low speed drive 644 is employed for final accurate adjustment of the conveyor to accurately position the test tube at the aspiration location (sensor 650). Switching between the two drives 644 and 646 is accomplished by the electronic switch 648 in response to a command signal outputted via the computer 608 and applied via I/O lines 654 to the switch 648.

Figure 21:
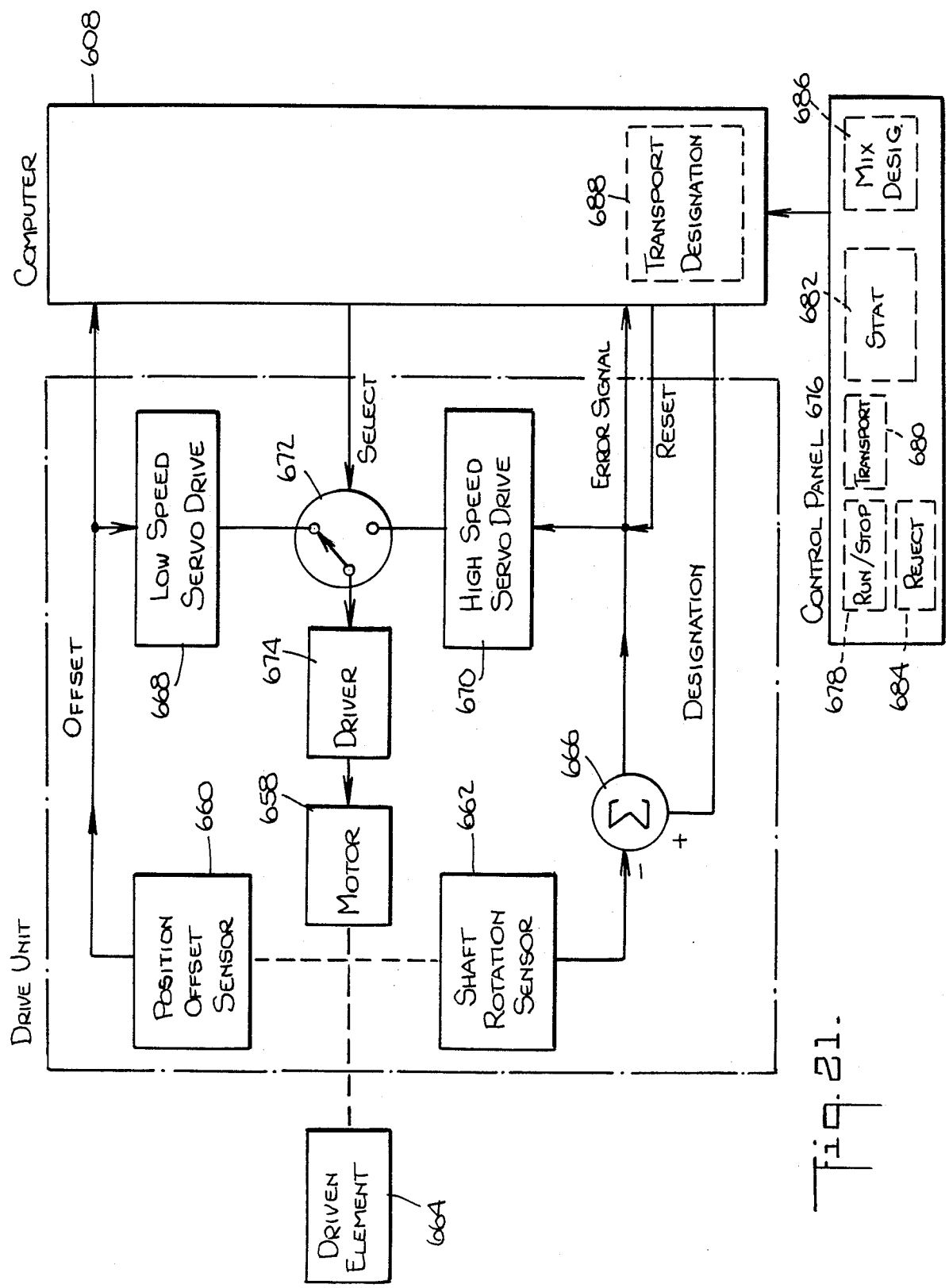
FIG. 21 is a simplified schematic diagram of the conveyor system.

A schematic configuration of the drive unit 656 which may be used for driving either the mix motor 624 or the transport motor 642 is shown in FIG. 21. It will be noted from FIG. 20 that the same configuration of closed-loop control using both high and low speed drives is employed for each of the motors 624 and 642. Both high speed drives are velocity profiled to maximize individual performance and obtain full movement of the air bubble through the fluid in the test tube.

FIG. 21 has been simplified by deletion of the I/O devices 610, and the bus 612 containing the I/O devices 610 with the computer 608, to more clearly show the connection between the drive unit 656 and the computer 608.

The drive unit 656 comprises a motor 658 mechanically coupled to a position offset sensor 660, a motor shaft rotation sensor 662 and a driven element 664. The description of the drive unit 656 is applicable to both the mixing system 604 and the transport system 606 of FIG. 20.

In the mixing system 604, the motor 658 and the driven element 664 respectively correspond to the table motor 624 and the mixing table. The sensor 660 corresponds to the sensor 634. Also included within the drive unit 656 is a summer 666 coupled to an output terminal of the shaft rotation sensor 662. The sensor 662 in combination with the summer 666 corresponds to the error signal output 636.

In the transport system 606 of FIG. 20, the motor 658 and the driven element 664 correspond respectively to the motor 642 and the conveyor. The sensor 660 corresponds to the sensor 650. The combination of the sensor 662 with the summers 666 corresponds to the error signal output 652.

Also included within the drive unit 656 is a low speed servo drive 668, a high speed servo drive 670, an electronic switch 672 and a driver 674. The servo drives 668 and 670 apply signals selectively via the switch 672 for activation of the motor 658. These signals are amplified by the driver 674 to a power level suitable for operation of the motor 658.

With reference to the mixing system 604, the servo drives 668 and 670 correspond respectively to the drives 626 and 628, the switches 672 corresponding to the switch 630. With respect to the transport system 606, the servo drive 668 and 670 correspond respectively to the drivers 644 and 646, the switch 672 corresponding to the switch 648. The switch 672 is operated by a command from the computer 608. An offset signal from the sensor 660 and an error signal from the summer 666 are applied as input signals to the computer 608. Also as shown in FIG. 21, a reset signal applied by the computer 608 for operation of the mixing system 604 is not used for the transport system 606.

Further shown in FIG. 21 is a control panel 676 of the system 600, the panel 676 including switches for operating the system 600. By way of example, the panel 676 includes a run/stop switch 678, a stat switch 682 for interrupting the operation of the system 600 to permit interchange of a test tube of relatively low priority on the mixing table with a test tube of relatively high priority.

The run/stop switch 678 permits an operator to restart the system after interchanging the test tubes. Also included on the panel 676 is a mix designation switch 686 to activate the mix cycle. Another switch designated reject 84 is used to stop and bypass unwanted samples. A further switch designated transport 680 is used to activate a one position at a time movement of the test tubes toward the aspirate position. A corresponding designation of position for the transport of the conveyor is provided by a read-only memory 688 in the computer 608. The amount of advancement of the conveyor is fixed in accordance with the physical size of the conveyor and is therefore not adjustable at the panel 676.

In operation of the drive unit 656, the computer 608 designates a desired position of the driven element 664 in terms of a number of motor shaft rotations. The desired position designation is applied as an input to the summer 666. The shaft rotation sensor 662 has a well known form including a pulse train generator providing in-phase and quadrature pulse trains in synchronism with rotation of the motor shaft, and an up/down counter which counts pulses of the pulse trains to output a signal to the summer 666 indicating the present position of the shaft.

The difference between the two signals is outputted by the summer 666 as a loop error signal which is applied via the high-speed servo drive 670 and the switch 672 to the driver 674. Similarly, the offset sensor 660 operates an offset signal to the low speed servo drive 668 which, in turn, via the switch 672, applies a signal to the driver 674 for operation of the motor 658. The offset sensor 660 may comprise an optical or Hall effect device for sensing the position of a moving vane (not shown in FIG. 21) coupled to the driven element 664, relative to a reference point. Movement of the vane to either side of the reference point generates a signal of corresponding sense (positive or negative) for driving the element 664 to the reference point.

Referring to FIGS. 20 and 21, the system 600 is described more fully as follows.

The aspiration system 602 is pneumatically operated in response to a set of valves which are individually actuatable by the computer 608 when a test tube or vial is present. The test tube sensor 638 detects that a test tube is in position for aspiration. The fill sensor 618 employs an electrical conductivity detector for signaling the computer 608 when the desired volume of blood has been aspirated from a test tube of the delivery system. When the needle has been fully retracted, the needle clear switch 620 signals the computer 608 that the needle is clear of the test tubes.

The motor 624 which positions the mix table and the motor 642 which drives the conveyor to transport the test tubes past the mix table are each DC servo motors which are driven by a variable speed electronic drive. The high speed servo drive 670 includes a well known velocity profile shaping circuit operative in a feedback loop to accelerate and decelerate the driven element 664, either the table or the conveyor, from a present position to a position designated by the computer 608. Upon receiving an indication of zero error, the computer 608 switches to the low speed servo drive 668 which operates in closed loop fashion in response to the mechanical vane of the offset sensor 660 to accurately locate the driven element 664 at a desired position. The offset sensor 660 signals the amount of offset to the computer 608, a zero offset indicating that the driven element 664 is in the desired position.

The circuit of the driver 674 imparts electric power to the motor 658 to drive the motor 658 either clockwise or counterclockwise. The driver 674 receives electrical signals via the switch 672 from either the high speed servo drive 670 or the low speed servo drive 668. The shaft rotation sensor 662, the summer 666 and the high speed servo drive 670 form a high speed feedback loop for driving the motor 658. The position offset sensor 660 and the low speed servo drive 668 form a low speed high precision feedback loop for driving the motor 658. The summer 666 between the shaft rotation sensor 662 and the high speed servo drive 670 provides for injection of the designated location of the driven element 664 by the computer 608, the output signal of the summer 666 serving as a loop error signal which is fed back to the computer 608.

In the operation of the mix table, the computer 608 may also provide a reset signal directly to the high speed servo drive 670 to move the table toward the home position, the offset sensor 660 indicating when the table has arrived in the vicinity of the home position. Thereafter, the low speed servo drive 668 can accurately position the table in the home position. The reset procedure is available for initializing the position of the table. On the control panel 676, the interrupt switch 682 enables one to stop the mixing operation wherein the table assumes a stat position in which a high priority test tube may be substituted for a lower priority test tube. Thereafter, the restart switch 684 is employed to continue the mixing operation.

Figure 22:
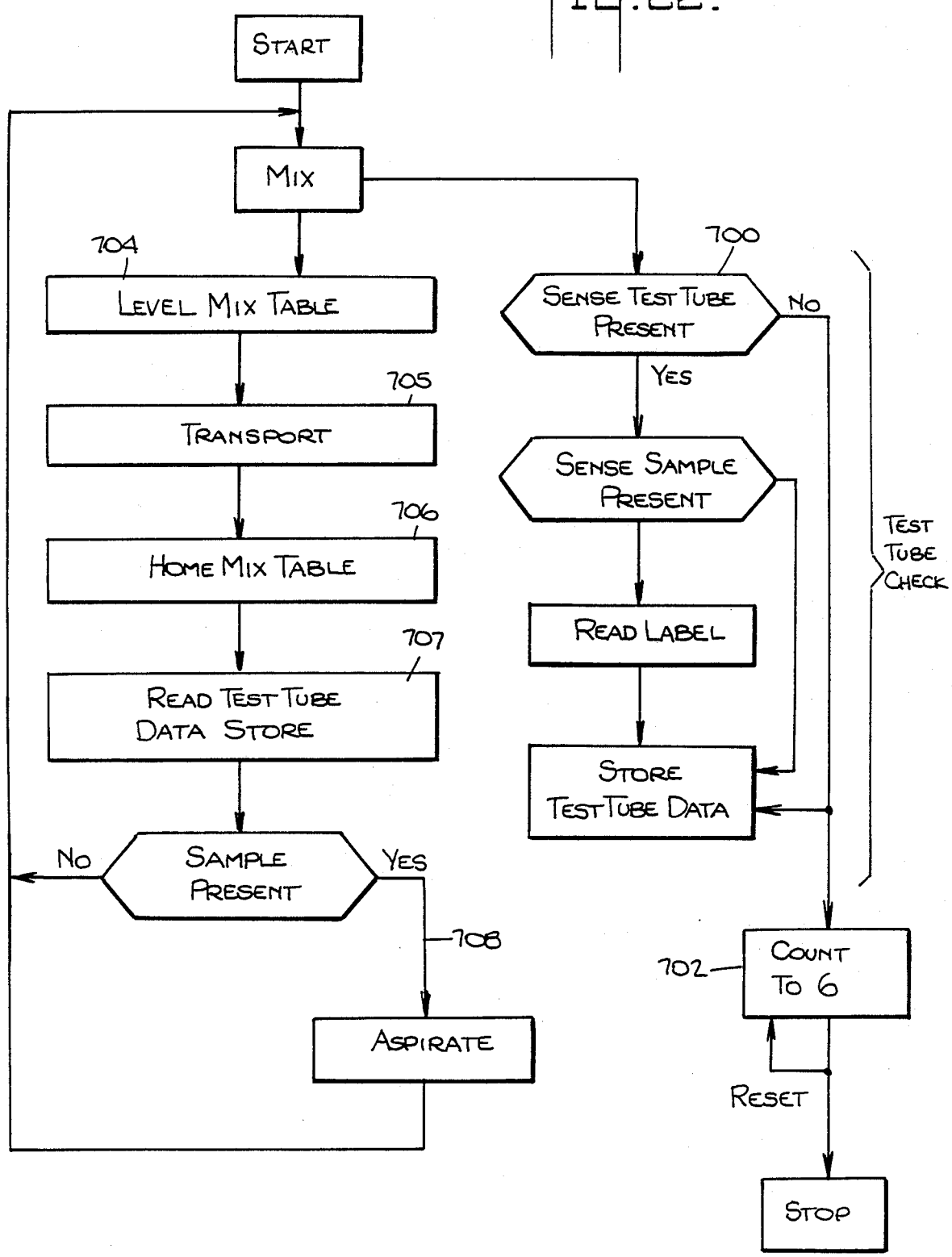
FIG. 22 is a simplified schematic diagram of the process of mixing and aspiration.
Figure 23:
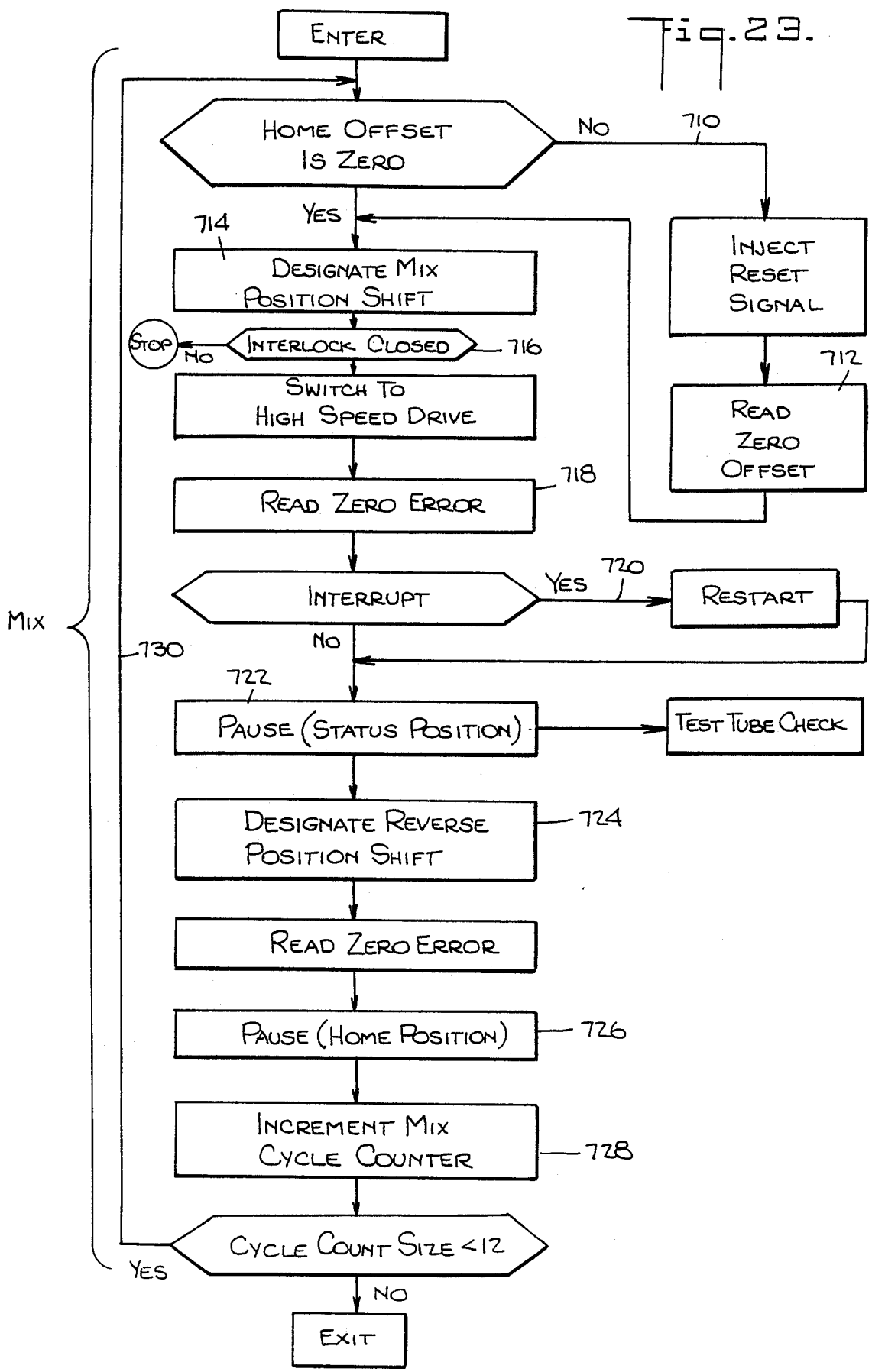
FIG. 23 is a detailed simplified schematic diagram of the mixing process.

Referring to FIG. 22, which shows a flow chart for operation of the delivery system, the cyclical procedure begins with a mixing operation that is shown schematically in FIG. 23. During the mixing operation, an opportunity is presented for sensing the presence of a test tube, its contents, as well as for reading a bar-code label on the test tube (Block 700). Thus, the presence and the fill status of each test tube is checked. In the event that no test tubes are present on six successive counts, representing six successive test tube holders (Block 702), the system shuts down on the assumption that there are no more blood samples to be checked.

After the mixing operation is complete, the mix table is placed in a level position (Block 704), the transport (Block 705) is activated to move the next test tube holder into position for aspiration, and the table is tipped back to the home position (Block 706) to access the aspirator. The computer 608 then checks stored test tube data (Block 707) to ascertain that a fluid sample is present, and if present (Line 708), activates the aspiration procedure. After aspiration, or if no fluid sample is present, the process returns to the mixing stage.

The mixing operation, as shown schematically in FIG. 23, begins at the home position of the mix table. If the mix table is not at the home position (Line 710), then the computer 608 injects a reset signal of relatively small value, as compared to large values of error signal which may be present in the high speed loop of the mix motor control. The reset signal drives the table toward the home position. The computer 608 terminates the reset signal upon a reading of zero offset (Block 712) from the offset sensor.

With the table in the home position, and with reference to the high speed drive 670 of FIG. 21, the computer 608 injects a signal at the summer 666 which designates a desired stat position of the table at the opposite extreme of tilt, the designated position being given in terms of shaft rotations of the mix motor 624. The personnel safety interlock is checked (Block 716), and if open, the program stops. If closed, the program continues with a switching of the driver input via switch 672 to the high speed servo drive 670 which activates the motor 658 to drive the table from the home position to the stat position. The computer 608 reads the error signal (Block 718) to determine when the stat position has been reached and also reads the control panel to determine if an interrupt signal has been entered.

If an interrupt signal has been entered (Line 720), the operation stops with the mix table holding the test tubes in the stat position. The stat position allows access to the test tube holders to replace one or more test tubes on the mix table with higher prior test tubes. After a test tube interchange has been completed on the mix table, the restart button is pressed to reactivate the system, at which point the mixing operation is resumed.

The mixing operation includes a pause (Block 722) in the stat position to allow an air bubble in the test tube to rise from the bottom of the test tube toward the top of the test tube. This enhances the mixing of blood or other fluids which are contained in the test tubes of the delivery system. The computer 608 then commands the mix table to return to the home position (Block 724) by injecting at the summer 666 a change in motor shaft rotation of the opposite sense to shift the table back to the home position. The servo loop operates to drive the motor 624 in the reverse direction. The computer 608 monitors the error signal. The attainment of a zero error indicates the table has returned to the home position. Thereupon, the computer 608 orders a pause (Block 726) to allow bubbles to rise through the fluid contained in the test tubes to accomplish a mixing of the fluid in the test tubes.

The foregoing description of the mixing process involves one complete cycle of motion of the mix table. A predetermined number of cycles is provided before a test tube is advanced one step along the conveyor. For example, there may be six locations on the mix table, with the mix table being cycled twelve times at each position, thus providing a total of 60 mixing cycles before the fluid in the test tube is aspirated.

As shown in the flow chart, the computer 608 counts the number of cycles (Block 728) and repeats (Line 730) the cyclical procedure until twelve cycles, for example, have been reached. At this point, the computer exits the mix routine to enter the transport phase of the operation.

A more detailed schematic form of the process steps shown in FIG. 22 of leveling (Block 704) and homing (Block 706) the mixing table is shown in FIG. 24. The transport phase of the operation is preceded by a leveling of the mixing table, and followed by a returning of the mixing table to the home position. Leveling of the mixing table is accomplished by activating the high speed motor drive 628 for the mixing motor 624 and by designating (Block 732) a number of motor shaft rotations which will pivot the table through an angle of 45 degrees to level the table. During activation of the motor, the error signal is read by the computer 608. A zero error signal (Block 734) indicates that the table has been brought to the level position. Thereupon, the transport process (Block 705), as shown schematically in FIG. 25, is initiated.

Following the transport process, the table is returned to the home position. This is accomplished by introducing the number of rotations of reverse motor direction (Block 736) into the summer 636 of the high speed servo motor drive 628. The high speed loop drives the motor 24 until a zero error is attained. After the computer 608 notes the presence of the zero error, the computer 608 operates the switch 630 to drive the mixing motor 624 via the low speed drive 626 (Block 738). In the low speed drive 626, the position of the motor 624 is accurately set with the aid of the optical or Hall-effect device sensor which signals the positional offset to the computer 608. The accurate positioning of the low speed drive 626 precisely locates a test tube for interfacing with the aspirator. Upon attaining zero offset, the computer 608 exits the transport routine to return to the main process schematically shown in FIG. 22.

The transport phase of the main process flow chart (Block 705 in FIGS. 22 and 24) is shown in a more detailed schematic form in FIG. 25. The high speed drive is employed with the transport motor 642. The computer designates (Block 740) the position of the next sprocket on the sprocket drive of the conveyor. After checking the personnel interlock, the program directs that the feedback loop of the high speed drive be switched (Block 742) to operate the transport motor 642. The transport motor 642 drives the conveyor one notch of the sprocket, to advance each of the test tubes by one position.

The attainment of a zero error signal indicates to the computer 608 that the conveyor has advanced to the next position. Thereupon, the computer switches the transport motor 642 to the low speed drive (Block 744) for highly accurate positioning of the conveyor to improve the interfacing of a test tube with the aspirator for accurate control of aspiration. The attainment of zero offset indicates to the computer 608 that a test tube holder on the conveyor has been placed in position for aspiration.

The computer control operation of the aspirator is shown in detailed schematic form in FIG. 26. First, the appropriate valve is actuated for direction of pneumatic fluid for advancing the needle-carrying carriage (Block 746) and centering cone toward a test tube in the aspirate position. The centering cone envelops an end of the test tube adapter to urge it and the test tube within, into alignment with the aspiration needle. Then, another valve is actuated for insertion of the needle (Block 748) through the rubber stopper of the test tube into the fluid contents of the test tube. Withdrawal of fluid is initiated to accomplish the aspiration. The fluid withdrawal continues until an electrical conductivity detector indicates, by generation of a fill signal (Block 750) that a container of fluid on the aspirator has received a predetermined amount of fluid. Thereupon, the computer 608 operates valves in the pneumatic system of the aspirator to terminate further withdrawal of fluid from the test tube. Termination of fluid withdrawal is followed by retraction of the needle (Block 752) and retraction of the carriage and centering cone. The needle clear signal (Block 754) indicates complete retraction of the needle so that further mixing and transport can be accomplished without interference. In response to the needle clear signal, a needle washing step is instituted and the program exits the aspirate procedure to return to the main flow procedure schematically shown in FIG. 22.

A system interlock switch 450 (FIG. 19) is engaged when the sampler 10 is in the FIG. 1 position and disengaged when the sampler 10 is in the FIG. 2 position. The sampler 10 is operational when the interlock switch 450 is engaged and nonoperational when the switch 450 is disengaged.

Some advantages of the present invention evident from the foregoing description include an automatic sampling system which incorporates a linkage that remains integral and continuous during mixing and transport cycles. The arrangement of the linkage permits the development of linkages of any selected length. A further advantage is the capability of the sampler to test samples from test tubes of different size and to provide accurate precise movement and positioning of test tubes relative to an aspiration needle.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A conveyor system for transporting test tubes to a sampling location of a test apparatus comprising,
   (a) a plurality of elongated test tube holders, with respective longitudinal axes, detachably joined together to form a continuous linkage, a test tube being receivable in and removable from each of said test tube holders,
   (b) latching means for detachably joining the test tube holders together to permit a first bi-directional pivotal movement between said test tube holders such that the longitudinal axis of one test tube holder is an axis of rotation for an adjacent test tube holder, whereby said linkage is flexible about the longitudinal axes of the respective test tube holders,
   (c) drive means for engaging the test tube holders of said linkage to move the linkage in a second direction past a sampling location,
   (d) mixing means for moving a first predetermined number of test tube holders in the linkage, separate from the other test tube holders in the linkage, in a predetermined pattern of movement, when said first predetermined number of test tube holders are in a first predetermined location with respect to a sampling location,
   (e) said latching means further including a pivot joint between adjacent test tube holders for permitting a second bi-directional pivotal movement between said adjacent test tube holders such that one of said adjacent test tube holders can be tilted about said pivot joint with respect to the other adjacent test tube holder whereby the longitudinal axis of said one adjacent test tube holder is inclinable with respect to the longitudinal axis of the other adjacent test tube holder, the inclinable bi-directional movement of said one adjacent test tube holder about said pivot joint with respect to the other adjacent test tube holder constituting said predetermined pattern of movement.

2. The conveyor system as claimed in claim 1 wherein a test tube of one size is engagable in one of said test tube holders and a test tube of another size is engagable in another of said test tube holders such that test tubes of different size are receivable in said linkage.

3. The conveyor system as claimed in claim 1 wherein said mixing means includes a table for supporting said first predetermined number of test tube holders and means for pivoting said table in said second bi-directional pivotal movement to cause the first predetermined number of test tube holders to simultaneously undergo said second bi-directional inclinable movement, said table being inclinable in positions respectively corresponding to a stat position and an aspirate position during said predetermined pattern of movement.

4. The conveyor system as claimed in claim 3 wherein said mixing means include means for stopping the second bi-directional movement of said table in said stat position t obtain access to any one of said predetermined number of test tube holders for removal and interchange of any one of the test tubes in the first predetermined number of test tube holders with a new test tube.

5. The conveyor system as claimed in claim 3 wherein said table is supported on a gear member, said gear member being motor driven in opposite directions to accomplish said second bi-directional pivotal movement.

6. The conveyor system as claimed in claim 1 wherein said test tube holder comprises an elongated tubular member and said latching means include a pivot member pivotally supported on said elongated tubular member for relative radial movement with respect to said tubular member about said longitudinal axis.

7. The conveyor system as claimed in claim 6 wherein said latching means further comprise a first latch member on said elongated tubular member and a second latch member on said pivot member.

8. The conveyor system as claimed in claim 7 wherein said first latch member of said one adjacent test tube holder is engagable with the second latch member of the other adjacent test tube holder to form said pivot joint.

9. The conveyor system as claimed in claim 1 wherein said test tube holders in said linkage have a generally circular periphery, and said drive means comprise at least one sprocket member having a plurality of cusp portions for engaging the periphery of said test tube holders to drive said linkage in said second direction.

10. The conveyor system as claimed in claim 9 wherein said drive means comprise two of said sprocket members, one of said sprocket members being positioned in advance of a sampling location and the other of said sprocket members being positioned beyond said sampling station.

11. The conveyor system as claimed in claim 1 including an entrance port through which said selected number of test tube holders continuously pass for movement by said drive means past a sampling location.

12. The conveyor system as claimed in claim 1 wherein said plurality of test tube holders comprise a second predetermined number of test tube holders.

13. The conveyor system as claimed in claim 12 wherein said second predetermined number of test tube holders is packed in an input cassette.

14. The conveyor system as claimed in claim 1 including an exit port through which said plurality of test tube holders continuously pass after passing a sampling location.

15. The conveyor system as claimed in claim 1 further including control means for controlling the movement of said linkage to permit a predetermined sequence of cycles of mixing and aspiration, wherein said linkage is rendered immobile in said second direction for predetermined time periods representing the duration of said mixing and aspiration cycles.

16. The conveyor system as claimed in claim 15 wherein said control means controls movement of said drive means when the mixing and aspiration cycles are completed to move said linkage a predetermined distance corresponding to the pitch of said test tube holders.

* * * * *